(12) United States Patent
Wilson et al.

(10) Patent No.: US 8,494,226 B2
(45) Date of Patent: Jul. 23, 2013

(54) SYSTEMS, METHODS AND DEVICES FOR USE IN ASSESSING CARCASS GRADING

(75) Inventors: Doyle E. Wilson, Huxley, IA (US); Viren R. Amin, Ames, IA (US)

(73) Assignee: Biotronics, Inc., Ames, IA (US)

( * ) Notice: Subject to any disclaimer, the term of this patent is extended or adjusted under 35 U.S.C. 154(b) by 961 days.

(21) Appl. No.: 12/435,683

(22) Filed: May 5, 2009

(65) Prior Publication Data

US 2009/0274804 A1 Nov. 5, 2009

Related U.S. Application Data

(60) Provisional application No. 61/050,533, filed on May 5, 2008.

(51) Int. Cl.
*A01K 43/00* (2006.01)
*G06K 9/00* (2006.01)

(52) U.S. Cl.
USPC .......................................... 382/110; 426/231

(58) Field of Classification Search
USPC ................... 382/110; 426/231, 442; 600/449
See application file for complete search history.

(56) References Cited

U.S. PATENT DOCUMENTS

| | | | |
|---|---|---|---|
| 5,079,951 A | 1/1992 | Raymond et al. | |
| 5,194,036 A | 3/1993 | Chevalier et al. | |
| 5,208,747 A | 5/1993 | Wilson et al. | |
| 5,303,708 A | 4/1994 | Stouffer | |
| 5,316,003 A | 5/1994 | Stouffer | |
| 5,339,815 A | 8/1994 | Liu et al. | |
| 5,353,796 A | 10/1994 | Schroeder et al. | |
| 5,452,722 A | 9/1995 | Langton | |
| 5,520,183 A | 5/1996 | Lake et al. | |
| 5,613,493 A | 3/1997 | Schafer | |
| 5,617,864 A | 4/1997 | Stouffer et al. | |
| 5,625,147 A | 4/1997 | Miles et al. | |
| 5,673,647 A | 10/1997 | Pratt | |
| 5,685,307 A | 11/1997 | Holland et al. | |
| 5,872,314 A | 2/1999 | Clinton | |
| 5,944,598 A * | 8/1999 | Tong et al. | 452/158 |
| 5,960,105 A * | 9/1999 | Brethour | 382/141 |
| 6,084,407 A | 7/2000 | Ellis | |
| 6,099,473 A | 8/2000 | Liu et al. | |
| 6,104,827 A | 8/2000 | Benn et al. | |
| 6,167,759 B1 | 1/2001 | Bond et al. | |

(Continued)

FOREIGN PATENT DOCUMENTS

EP 1026516 B1 4/2006

OTHER PUBLICATIONS

R.K. Johnson, E.P. Berg, R. Goodwin, J.W. Mabry, R.K. Miller, O.W. Robinson, H. Sellers, and M.D. Tokach. Evaluation of procedures to predict fat-free lean in swine carcasses. J. of Anim. Sci. 2004. 82:2428-2441.

(Continued)

Primary Examiner — Amara Abdi

(57) ABSTRACT

Methods, systems and devices are implemented in connection with measuring the relative content of intramuscular fat (IMF) in a portion of muscle tissue. Consistent with one such method a probe is presented to the portion of muscle tissue. The probe produces a response-provoking signal in the muscle tissue. A resulting signal is used to determine the relative content of IMF in the portion of muscle tissue as a function of the pressure being exerted between the probe and the portion.

2 Claims, 18 Drawing Sheets

U.S. PATENT DOCUMENTS

| | | | |
|---|---|---|---|
| 6,170,335 B1 | 1/2001 | Clinton | |
| 6,198,834 B1* | 3/2001 | Belk et al. | 382/110 |
| 6,200,210 B1 | 3/2001 | Pratt | |
| 6,322,508 B1 | 11/2001 | Goldenberg et al. | |
| 6,591,681 B1 | 7/2003 | Shimada et al. | |
| 6,730,034 B1* | 5/2004 | Lang et al. | 600/449 |
| 7,088,862 B1* | 8/2006 | Silver et al. | 382/199 |
| 7,203,911 B2 | 4/2007 | Williams | |
| 2004/0125987 A1* | 7/2004 | Haagensen et al. | 382/110 |
| 2007/0043290 A1 | 2/2007 | Goepp et al. | |
| 2007/0237423 A1* | 10/2007 | Tico et al. | 382/284 |
| 2008/0031506 A1* | 2/2008 | Agatheeswaran et al. | 382/132 |

OTHER PUBLICATIONS

Y. Liu and J.R. Stouffer. Pork carcass evaluation with an automated and computerized ultrasonic system. J. of Anim. Sci. 1995. 73:29-38.

D. Black, J. Vora, M. Hayward, and R. Marks. Measurement of subcutaneous fat thickness with high frequency pulse ultrasound: comparisons with a caliper and a radiographic technique. Clin. Phys. Physiol. Meas. 1988, vol. 9, No. 1,57-64.

National Pork Producers Council (NPCC). 2001. Pork Quality. National Pork Procedures Council, P.O. Box 10383, Des Moines, IA.

Amin V, D. Wilson, R. Roberts, and G. Rouse, "Tissue characterization for beef grading using texture analysis of ultrasonic images," *Proc. of 1993 IEEE Ultrasonic Symposium*, pp. 969-972, 1993.

Bondestam S, A. Alanen, and S. Toikkanen, "Correlations of liver echo intensity with cytology and chemical measurements of fat, water and protein content in live burbots (*Lota lota*)," *Ultrasound in Med. and Boil.* 18, pp. 75-50,1992.

Haberkorn U, I. Zuna, A. Lorenz, H. Zerban, and G. Layer, "Echographic tissue characterization in diffuse parenchymal liver disease: Correlation of image structure with histology," *Ultrasonic Imaging* 12, pp. 155-170, 1990.

Haralick RM, K. Shanmugam and I. Dinstein, "Textural features for image classification," *IEEE Trans. Sys. Man. Cyberm*. 3, pp. 610-621, 1973.

Layer G, I. Zuna, A. Lorenz, H. Zerban, and U. Haberkorn, "Computerized ultrasound B-scan texture analysis of experimental fatty liver disease: Influence of total lipid content and fast deposit distribution," *Ultrasonic Imaging* 12, pp. 171-188, 1990.

Layer G, I. Zuna, A. Lorenz, H. Zerban, and U. Haberkorn, "Computerized ultrasound B-scan texture analysis of experimental diffuse parenchymal liver disease: Correlation with histology and tissue composition," *Jn. Clin. Ultrasound* 19, pp. 193-201,1991.

Nicholas D, D. Nassiri, P. Garbutt, and C.R. Hill, "Tissue characterization from ultrasouind B-scan data," *Ultrasound in Med. and Biol*. 12, pp. 135-143, 1986.

Unser M. Texture classification and segmentation using wavelet frames. 1995. IEEE Transactions on Image Processing, 4:1549-1560.

Amin V, Wilson D, Rouse G, and Zhang H. 1995. Computerized ultrasound system for on-line evaluation of intramuscular percentage fat in *longissimus dorsi* muscle at a commercial packing facility. 1995 Beef Research Report, Iowa State University, Ames, Iowa.

Brondum, J. M. Egebo, C. Agerskov and H. Busk. 1998. On-line pork carcass grading with the Autofom ultrasound system. J. Anim. Sci. 1998. 76:1859-1868.

Faucitano, L., P. Huff, F.T. Teuscher, C. Gariepy and J. Wegner. 2005. Application of computer image analysis to measure pork marbling characteristics. Meat Sci. 69:537-543.

Hassen, A., D.E. Wilson, V. Amin, G. H. Rouse, and C.L. Hays. 2001. Predicting percentage of intramuscular fat using two types of real-time ultrasound equipment. J. Anim. Sci, 79:11-18.

Izquierdo, M.M., V.R. Amin, D.E. Wilson and G. H. Rouse. 1996. Models to predict intramuscular fat percentage in live beef animals using real-time ultrasound and image parameters: Report on data from 1991 to 1994. A.S. Leaflet R1324, Dept. Anim. Sci., Iowa State Univ., Ames, IA.

National Pork Board (NPB). 1999. Pork Quality Standards. National Pork Board, P.O. Box 9114, Des Moines, IA.

Newcom, D.W., T. J. Baas, and J.F. Lampe. 2002. Prediction of intramuscular fat percentage in live swine using real-time ultrasound. J. Anim. Sci. 80:3046-3052.

Morlein, D., R. Rosner, S. Brand, K.-V. Jenderka, and M. Wicke. 2004. Non-destructive estimation of the intramuscular fat content of the longissimus muscle of pigs by means of spectral analysis of ultrasound echoes. J. Meat. Sci. 69:187-199.

Schwab, C.R. and T.J. Baas. 2006. Development of a model to predict intramuscular fat in live pigs using real-time ultrasound. Iowa State University Animal Industry Report 2006, A.S. Leaflet 2050.

Wilson, D.E., H.L. Zhang, G.H. Rouse, D.A. Duello and M.M. Izquierdo. 1992. Prediction of intramuscular fat in the *longissimus dorsi* of live beef animals using real-time ultrasound. J. Anim. Sci. 70(Suppl. 1):224.

Silva, S.R., Afonso, J.J., Santos, V.A., Monteiro, A., Guedes, C.M., Azevedo, J.M.T., and Dias-da-Silva, A. 2006 In vivo estimation of sheep carcass composition using real-time ultrasound with two probes of 5 and 7.5 MHz and image analysis. J. Anim. Sci. 84:3433-3439.

Miller, D.C., 1998 Accuracy and Application of Real-Time Ultrasound for Evaluation of Carcass Merit in Live Animals, Department of Animal Science, NCSU.

Schinckel, A.P., Lofgren D.L., Stewart, T.S. 2000 Impact of Measurement Errors on Predicting Pork Carcass Composition: Within Sample Evaluation. Department of Animal Sciences, Purdue University.

Davis, J.K., Temple, R.S., and Mccorrmick, W.C. 1996 A Comparison of Ultrasonic Estimates of Rib-Eye Area and Fat Thickness in Cattle. J. Anim. Sci. 25:1087-1090.

Williams, A.R. 2002 Ultrasound applications in beef cattle carcass research and management. J. Anim. Sci. 80(E. Suppl. 2): E183-E-188.

Wilson, D.E. 2007 Use of Real-Time Ultrasound in % IMF Prediction for Swine. Biotronics Inc.

Kim N, V. Amin, D. Wilson, G. Rouse, and S. Udpa, "Ultrasound image texture analysis for characterizing intramuscular fat content of live beef cattle," Ultrasonic Imaging, 20:191-205.

\* cited by examiner

SYSTEMS, METHODS AND DEVICES FOR USE IN ASSESSING CARCASS GRADING

RELATED DOCUMENTS

This patent document claims the benefit, under 35 U.S.C. §119(e), of U.S. Provisional Patent Application Ser. No. 61/050,533 filed on May 5, 2008, and entitled "SYSTEMS, METHODS AND DEVICES FOR USE IN ASSESSING MUSCLE TISSUE QUALITY;" this patent document and the Appendices filed in the underlying provisional application are fully incorporated herein by reference.

FEDERALLY SPONSORED RESEARCH OR DEVELOPMENT

Subject matter described in this document is based upon work supported by the Cooperative State Research, Education, and Extension Service, U.S. Department of Agriculture, under Agreement Nos. 2006-33610-16761 and 2007-33610-18441. The U.S. government may have certain rights to the invention.

FIELD OF THE INVENTION

The present invention relates to systems and methods for inspecting and measuring muscle tissue parameters, such as fat and lean content and quality of muscle tissue.

BACKGROUND

There are several attributes of muscle tissue quality that relate to palatability and consumer eating satisfaction. Assessments of such qualities can be useful for a variety of food animals. Such assessments can also be useful in both live animals and animal carcasses. For example, one such important attributes is the amount of intramuscular fat (IMF) that exists in the longissimus dorsi muscle. Within the U.S., the longissimus dorsi muscle or "loin" is a very high value part of the pork carcass. IMF in the pork loin adds significantly to flavor and juiciness, traits that are highly related to eating satisfaction. The amount of the IMF in the pork loin is governed by genetics, age of the animal at time of harvest and to a lesser degree by other environmental factors and animal nutrition.

There is considerable variation in IMF from animal to animal or from carcass to carcass with mean values in the range of 2.0-2.5%. Carcasses with less than 2.0% IMF can be undesirable. Carcasses with more than 3.5% IMF are valued by high-end restaurant chefs that offer pork on their menus. Carcasses with more than 6% IMF are highly valued in some foreign markets, such as in Japan. Because of these market differences, the ability to noninvasively measure the amount of IMF in the pork loin has value to the pork packing plant as well as to other aspects of the muscle tissue-processing industry.

A significant challenge to measuring IMF in the packing plant is the speed by which carcasses are processed. As an example, with many plants running their chain speed at 1200 carcasses per hour, a carcass would be measured in less than 2 seconds if the carcass is going to be measured during the packing process. In addition, pork carcasses are not routinely split anywhere along the loin that would expose the internal tissue for either a subjective or quantitative measure of the amount of IMF in the lean tissue. Consequently, packing plants can benefit from efficient and practical methods of noninvasively "looking" inside the loin muscle and determining the percentage of IMF as compared to the amount of lean tissue.

SUMMARY

The present invention is directed to systems and methods for inspecting aspects, such as content and quality of muscle tissue. These and other aspects of the present invention are exemplified in a number of illustrated implementations and applications, some of which are shown in the figures and characterized in the claims section that follows.

Consistent with an embodiment of the present invention, a method is implemented for measuring the relative content of intramuscular fat (IMF) in a portion of muscle tissue. A probe is presented to the portion of carcass skin covering subcutaneous fat and the muscle tissue. The probe produces a response-provoking signal in the muscle tissue. A resulting signal is used to determine the relative content of IMF in the portion of muscle tissue as a function of the pressure being exerted between the probe and the portion.

Consistent with another embodiment of the present invention, a system measures the relative content of intramuscular fat (IMF) in a portion of muscle tissue. A probe carries a response-provoking signal to the portion of muscle tissue. A pressure sensor senses pressure being exerted between the probe and the portion. A data processor measures the relative content of IMF in the portion of muscle tissue. The relative content of IMF is determined as a function of the response-provoking signal and the sensed pressure.

In a specific embodiment, the resulting signal is used to filter captured images that fall outside of an acceptable pressure range. For example, image capture can be limited to only capture while the pressure is within the acceptable range or captured image data can be stored and screened thereafter. In another example, the captured image data can be analyzed by weighting or otherwise adjusting the IMF calculations according to the resulting signal (e.g., by accounting for the pressure in the calculations or reducing the significance of data from images associated with certain pressure levels).

The above overview is not intended to describe each illustrated embodiment or every implementation of the present invention. The figures and detailed description that follow and in the appended claims, more particularly exemplify these embodiments.

BRIEF DESCRIPTION OF THE DRAWINGS

The invention may be more completely understood in consideration of the detailed description of various embodiments of the invention that follows in connection with the accompanying drawings in which.

Figure 1A:
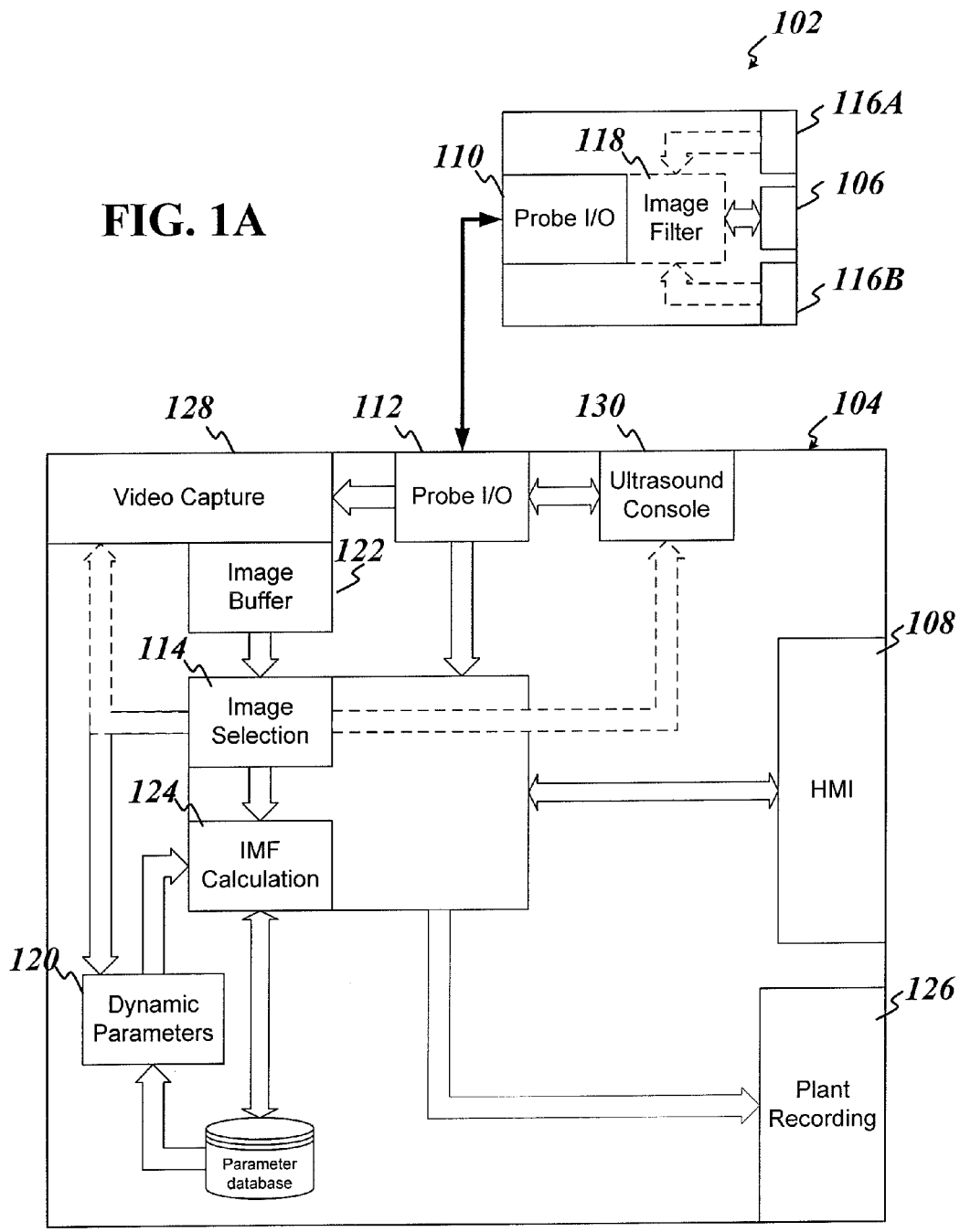
FIG. 1A shows a system-level diagram, consistent with an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for inspecting and measuring muscle tissue parameters, such as fat and lean composition and quality of muscle tissue. The muscle tissue can originate from any number of different food animals and the inspection and measuring can be obtained from live swine or pork carcasses. A specific embodiment of the present invention facilitates measurement of intramuscular fat (IMF) of a pork carcass. Unless otherwise stated, the term "animal" refers to either a live animal or an animal carcass. While the present invention is not necessarily limited to such applications, various aspects of the invention may be appreciated through a discussion of various examples using this context.

An embodiment of the present invention is directed toward a noninvasive mechanism for determining IMF content of muscle tissue, such as muscle tissue from live pork animals or pork carcasses. Ultrasound imaging is used to capture internal images of the muscle tissue. An image processor processes the images using algorithms specifically selected and/or tailored to use with the particular muscle tissue (e.g., the type of food animal or whether live or dead) to determine the IMF content.

Specific embodiments of the present invention are directed toward facilitating the determination of pork loin IMF content in a pork-carcass processing line (e.g., in a muscle tissue packing plant). Devices, methods and systems facilitate IMF content determinations at speeds and accuracy levels that are particularly useful for use on a processing line. Various aspects include, for example, streaming image capture, image selection criterion, specifically tailored algorithms and/or facilitating proper contact between the carcasses and a probe.

One other aspect of the present invention involves the use specially designed algorithms with carefully selected parameters. These algorithms and their parameters provided surprisingly accurate results. Use of these algorithms and parameters, discussed in more detail below, have resulted in surprisingly accurate and efficient tissue characterization. Moreover, embodiments of the present invention are built upon the realization that filtering of the image data or filtering of parameters from the image data can be particularly useful for real-time applications that demand highly accurate characterizations of muscle tissue.

Embodiments of the present invention provide IMF content measurements using ultrasound imaging. These measurements are surprisingly consistent with even objective chemical-based measurements of IMF content.

Embodiments of the present invention facilitate proper placement of an ultrasound transducer on the skin of the carcasses. The inventors have recognized and appreciated that accurate IMF measurements can be obtained by ensuring that images used in determining the IMF content are taken with the proper pressure between the ultrasound transducer and the carcass skin. In a specific embodiment, one or more pressure sensors are used to provide feedback regarding the pressure between the ultrasound transducer and the pork carcass skin.

Embodiments of the present invention are directed toward the use of image processing to determine the IMF content of pork carcasses. Quantitative parameters of ultrasound/tissue interaction used for such image processing include, but are not limited to, signal strength, distribution, and scattering. Aspects of the present invention are directed to facilitating the derivation of such quantitative parameters. Image processing methods such as texture analysis indirectly provide information about the tissue scattering. IMF deposits cause the ultrasonic waves to scatter. Constructive and destructive interference of waves from such scattering produces graininess, or a textural pattern, in ultrasound images. These patterns are affected by properties of the IMF deposits such as size, density, and distribution.

The present inventors have recognized and appreciated that the distinct texture pattern produced in ultrasound images based on the content and distribution of IMF may be used to objectively and non-invasively estimate IMF automatically, in real time, and at line speed.

An embodiment of the present invention is directed toward a noninvasive system for measuring the percentage IMF along with subcutaneous fat depth and muscle depth in the longissimus dorsi muscle of hot carcasses. The measurements are made real-time on carcasses that are moving on a transport rail at a nearly constant rate of 1,200 carcasses per hour.

Measurements are made from live video-streaming ultrasound images as the carcasses move past a scanning station. The scanning station can be fully automated, manual or a combination thereof.

System output data is interfaced with the packing plant individual carcass identification system and hot carcass weighing scale. The combined data is used by the plant to determine individual carcass value and can be useful for differentiating and sorting of each carcass for alternative fabrication and processing of wholesale pork products within minutes after harvest.

Embodiments of the present invention are also suitable for determining IMF or other muscle tissue characteristics of live animals such as live swine. Because IMF and other muscle tissue characteristics are at least in part dependent on genetics, measuring live or recently harvested animals may produce data to facilitate breeding processes, feeding or care regimens, and so forth aimed at achieving a higher yield of livestock exhibiting desired muscle tissue characteristics.

By way of example, FIG. 1 illustrates a system for use in inspecting and measuring muscle tissue parameters in carcasses, according to an embodiment of the present invention. Probe 102 communicatively connects to processing block 104 using probe input/output (/O) 110, 112. This connection can be implemented using, for example, a wired connection, wireless connections or a removable storage medium. Wired connections can be implemented using any suitable (e.g., bandwidth and reliability) protocol including, but not limited to, universal serial bus (USB), IEEE 1394 and Ethernet. In a specific instance, the probe is connected using a data-carrying cable (e.g., electrical or optical). In another instance, the probe is integrated into a single device that includes the processing block 104. Wired connections can also be implemented using a more temporary connection, such as a removable data storage device or a cradle for placement of the probe. Wireless connections for non-ultrasound communications can be implemented using an assortment of different techniques and protocols including, but not limited to, 802.11x or ultra-wideband (UMB).

Probe 102 provides images of the carcass using ultrasound imaging. An ultrasound transducer 106 converts control data into transmitted sound and received sound into image data. In a specific example, the transducer is a piezoelectric transducer that converts between electrical and physical vibration energy. Embodiments of the invention are designed to allow use of a variety of existing or future imaging techniques (e.g., other than piezoelectric transducers). The actuation of such transducers can be controlled by ultrasound controller 130. For example, controller 130 can provide a stimulus profile for capturing a series of images from the same carcass.

Embodiments of the invention include a human-machine interface (HMI) 108. HMI 108 facilitates operation, monitoring or otherwise interfacing with the system by a human operator.

Image selection block 114 is an optional component that selects between a set of images obtained from the probe 102. Image selection block may facilitate the selection of images based on direct or secondary indicia of image quality or usability. For example, acquired images may be screened for blurriness, the existence or absence of certain features, the existence or absence of one or more subset regions of interest (ROI) within the image, and for conditions under which the images were acquired.

With respect to image acquisition conditions, it has been observed that the quality and repeatability of ultrasonic images acquired from animal carcasses can be affected by the pressure applied between the probe transducer and the carcass skin. Thus, in reference to FIG. 1A, the probe 102 optionally includes one or more pressure sensors such as load cells 116A and 116B. Information from the pressure sensors may be used by an image filter 118 within the probe 102 to decide whether to capture and transmit images to the processing block 104. In other embodiments, the pressure data is transmitted to the processing block 104 for analysis, at which point the images may be recorded using video capture 128 and/or buffer 122 and retained for further analysis or discarded based on the pressure readings. In another example, the processing block 104 analyzes the pressure data and in response determines whether or not to activate the ultrasound transducer. Feedback signals may be provided to control further image acquisition by the probe and/or to provide an operation status indication (e.g., yellow light for non-acquisition stand-by mode when the probe is not applied or insufficient pressure is applied, red light for non-acquisition based on too much pressure or unbalanced pressure, and green light for ultrasonic activation and image acquisition due to proper application of the probe).

During image selection screening, images are removed or discarded if the quality and/or pressure criteria are not met. In certain embodiments, images discarded based on such screening may be stored for later analysis, for example, to facilitate system diagnostics, for adjusting of screening algorithm parameters, and so forth.

According to specific embodiments of the present invention, the processing parameters 120 used by the algorithms for determining IMF percentage estimates can be dynamically adjusted for each carcass. For example, each carcass has a specific makeup with regards to the tissue depths of various tissue types. These differences can affect the captured image data as, for example, different tissue types can exhibit different sound propagation properties. Tissue types that can be monitored for dynamic adjustments include, but are not limited to, subcutaneous fat, muscle (loin), skin and bones. In a specific instance, the subcutaneous fat depth and loin depth within a region of interest are determined. These determined depths are then used as parameters in the algorithms for the specific carcass.

The IMF percentage determination 124 can be provided for immediate viewing using HMI 108 and/or recorded 126 for future use (e.g., sorting, recording, pricing and feedback for genetic profiling).

Aspects of the invention are directed to calibration of the device. The calibration can be particularly useful for maintaining consistency between measurements where, for example, components of the device are replaced or operation parameters change (e.g., changes over time due to use or due to temperature variations). One mechanism for calibration involves the use of a default device that is already calibrated. Measurements are taken for each device and the parameters for the device under calibration are modified so that the IMF readings coincide with the IMF readings of the default device. Another mechanism involves the use of a known item from which IMF readings are taken. The item could be one or more carcasses. The measured IMF readings for the device under calibration can be compared to the actual IMF values of the carcasses. Alternatively, the item could be a specially constructed test apparatus. The apparatus can be constructed to test the response parameters of the device under calibration (e.g., using materials having a variety of densities and thicknesses and/or simulating a carcass). The readings from the device under calibration can be used to define the particular response characteristics and to modify the algorithms accordingly. Another aspect of calibration can include stimulus profiles that define how the probe is activated during the calibration process.

Aspects of the present invention relate to selection of a region of interest (ROI) within image(s) captured by the probe. Such a selection of an ROI can be particularly useful for reducing the computational power needed to process the image(s) and/or for improving the accuracy of IMF calculations by excluding less-than-ideal portions of the image.

Figure 1B:
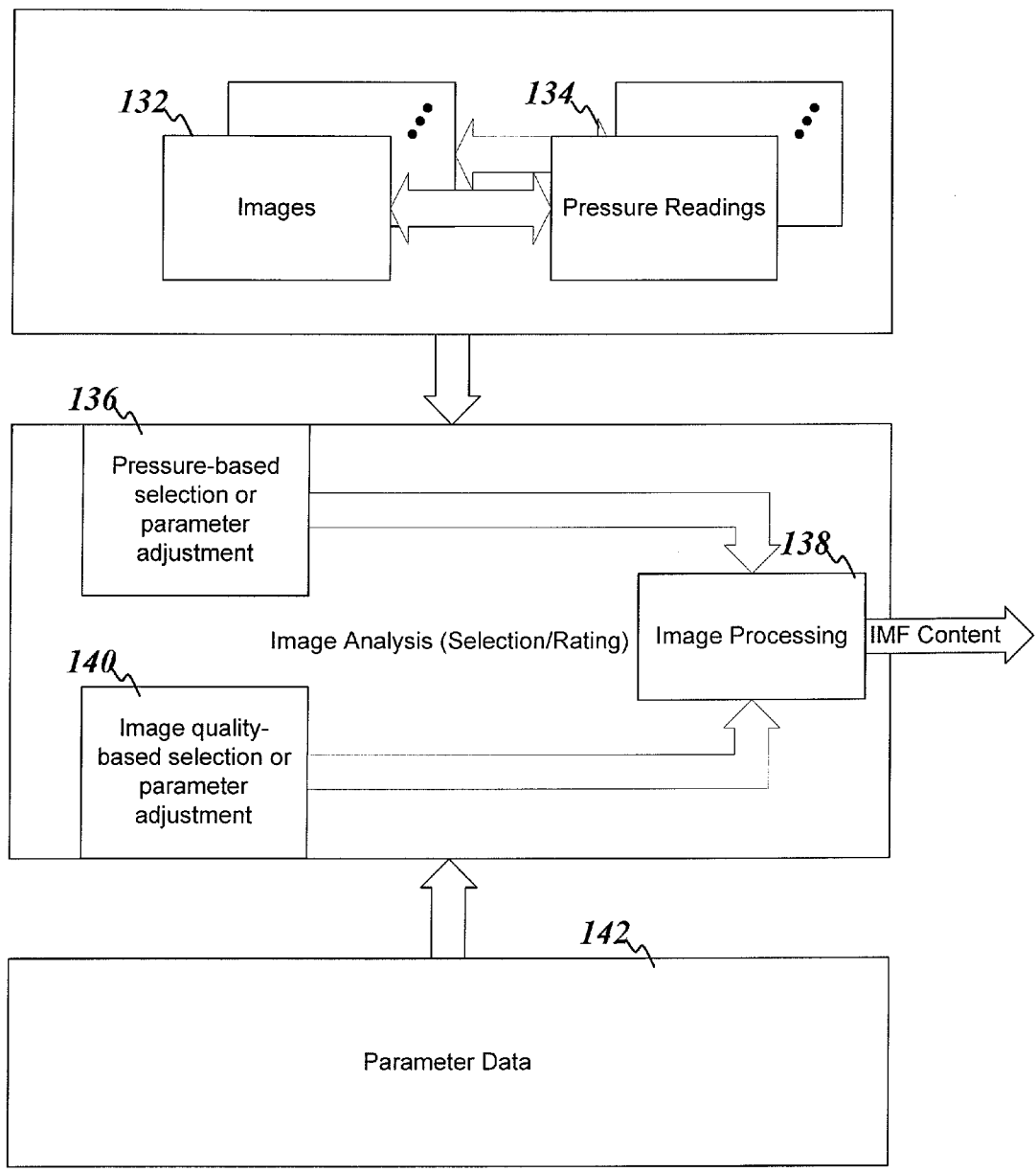
FIG. 1B shows a flow diagram for determining IMF content, consistent with an example embodiment of the present invention.

FIG. 1B shows a flow diagram for providing an IMF content estimation, according to an example embodiment of the present invention. The system stores a set of images obtained from a carcass 132. These images can be associated with pressure readings 134. The association can be an explicit data bit stored with the images (e.g., database association or tag added to the images) or can be implicit due to filtering of the images prior to storage (e.g., the act of storing implies that the images fall within the desired pressure range). Image processing 138 involves use of the set of images 132 to calculate the IMF percentages. One component of image processing 138 involves parameter data 142. Other components can include, for example, pressure-based selection or parameter adjustment 136 and/or image quality-based selection or parameter adjustment 140. Each of these components 136 and 140 can be used to exclude various images, such as those that do not meet pressure or image quality criterion. Alternatively, (or in addition to such image exclusion), components 136 and 140 can be used to modify the parameters 142 for respective images. In one instance, this modification can take the form of reduction in the statistical contribution of images with less-than-ideal pressure readings or having low-quality of image (e.g., blurred images or images with poor contact). In another instance, the modification can include compensations to the parameter data 142. For example, images associated with certain low pressure readings may result in incorrect IMF content determinations. Where such incorrect IMF content determinations deviate from the actual IMF content by a predictable amount, the determinations can be adjusted accordingly.

Figure 2:
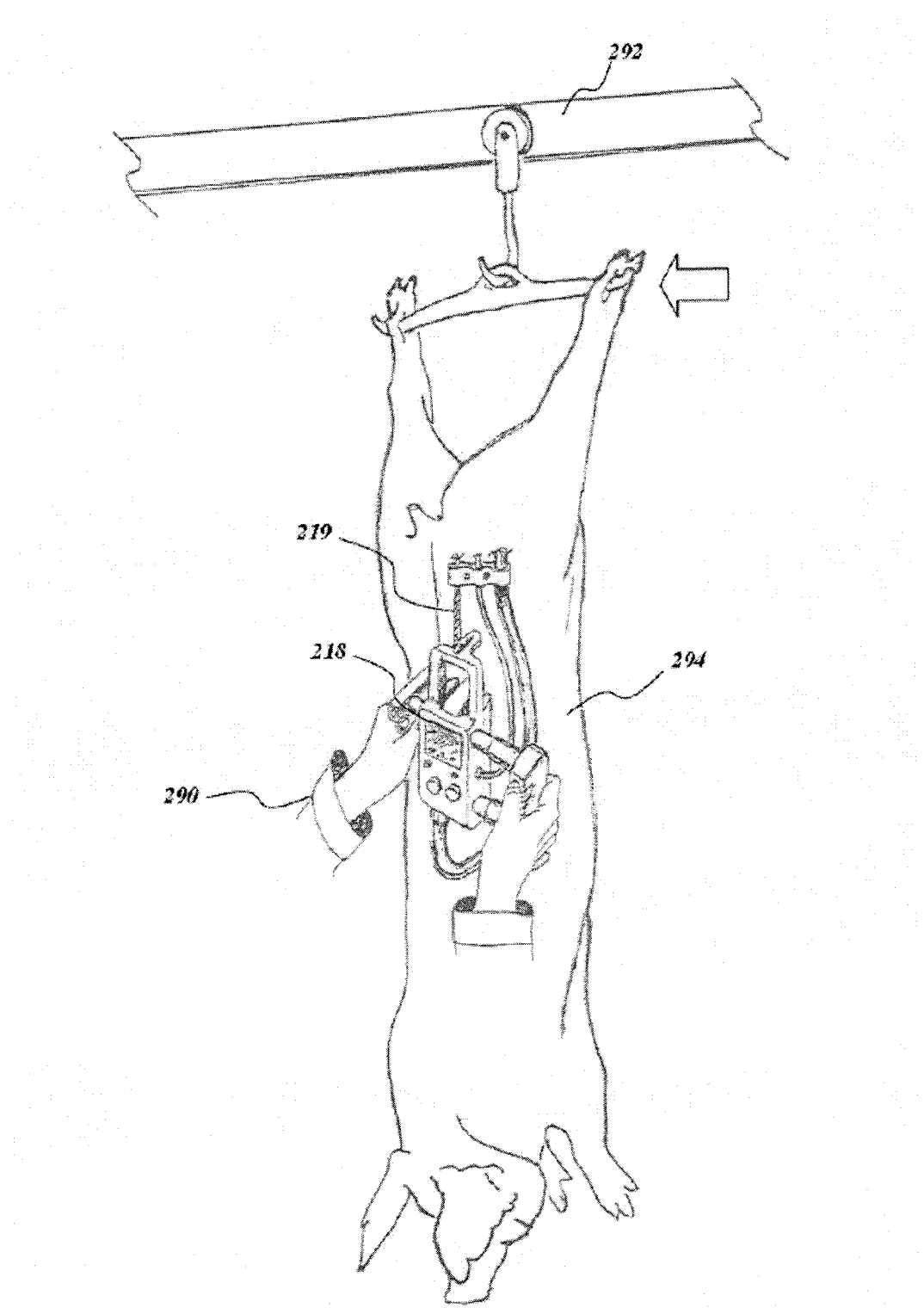
FIG. 2 illustrates ultrasonic scanning of a hot carcass within a packing plant environment, consistent with an example embodiment of the present invention.

By way of example, FIG. 2 illustrates a packing plant environment where hot carcasses, such as carcass 294, are conveyed along an overhead conveyor system 292 in a direction indicated by the arrow. As the carcasses pass an operator measurement position, an operator 290 applies an ultrasonic transducer probe from ultrasound system 218 to a specified portion of the carcass 294. Images acquired from the ultrasound system 218 are provided via connection 219 to a data acquisition system for data analysis.

Systems in accordance with certain embodiments include a hardware subsystem that includes I/O components for obtaining data from a carcass and for interfacing with an operator. A data processing subsystem includes components for screening and processing data and for providing results for output. While a number of different implementation options exist (e.g., the data processing subsystem may be suitably implemented using hardware circuitry, programmable logic devices, firmware, software, and combinations thereof), the following description provides a specific implementation as an exemplary system.

Figure 3A:
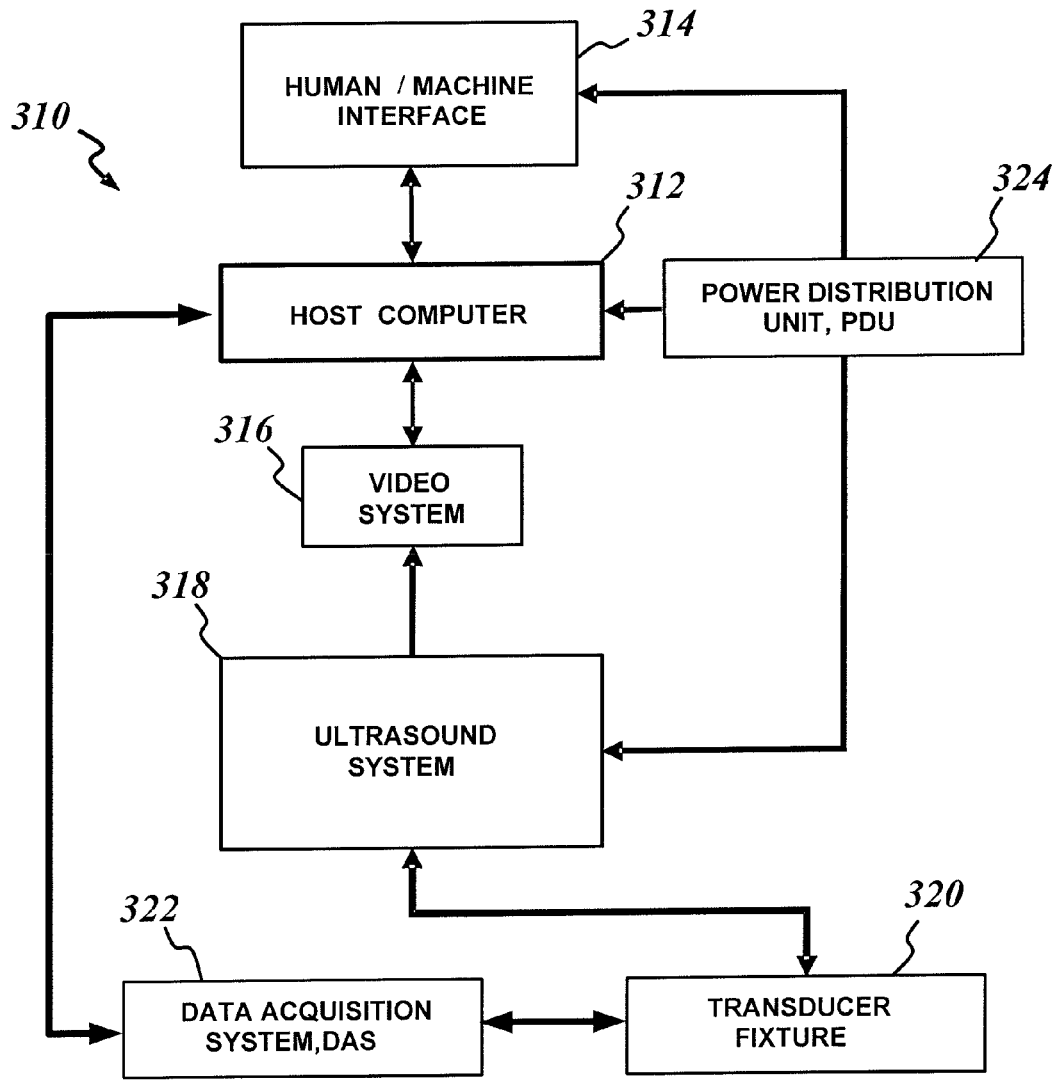
FIG. 3A shows an exemplary hardware subsystem, consistent with an example embodiment of the present invention.

The hardware subsystem includes components for use in the capture of ultrasound data in the form of video images, for example, for online processing of animal carcasses. The hardware subsystem may be implemented as a highly-portable, rugged equipment enclosure with incorporated electrical and electronic components. An exemplary hardware subsystem 310 is illustrated in FIG. 3A, with various component systems shown in additional detail in FIGS. 3B, 3C and 3D. Hardware subsystem 310 includes a host computer 312, an ultrasound system 318 coupled to transducer fixtures 320, an operator interface 314, a video system 316, a data acquisition system 322, and a power distribution unit 324. The host computer 312 may provide a platform on which to run the software subsystem.

An operator interacts with the system through the human-machine interface 314. Power distribution unit (PDU) 324 distributes electric power, for example from utility power mains, to various sub units. In addition to providing a switch for normal power up and power down, the PDU may prevent poor-quality electrical power from reaching the sensitive electronic components within the hardware subsystem 310.

Data acquisition system 322 gathers information from force sensors incorporated into the ultrasound transducers to determine proper positioning and pressure of the ultrasound probe on the carcass skin. Feedback signals may be generated for the operator to view, for example, using light-emitting diodes (LEDs) to indicate a probe status, such as the ultrasound probe is ready to scan the carcass, the ultrasonic probe is properly positioned (e.g., the correct amount of pressure), the ultrasonic probe is improperly positioned (e.g., the incorrect amount of pressure), data acquisition is in progress, data acquisition has ended, and so forth.

In certain embodiments, ultrasound system 318 includes a portable veterinary ultrasound scanner console and a hand-held ultrasound probe (or transducer). The ultrasound system 318 creates an image from sound by producing a sound wave, receiving echoes, and interpreting those echoes. In a specific example, the ultrasound probe uses a piezoelectric portion that resonates at the desired frequency by electrical pulses from the ultrasound scanner console. Sound waves are received again by the transducer after interacting with the carcass sample. The console assembles video images from these echoes. Video images from the console are sent to the video system 316 to be routed and digitized before being sent to the host computer 312 in the form of individual video frames.

In certain embodiments, video system 316 includes a frame grabber and video input/output (I/O) connection hardware. The frame grabber captures individual video frames so that digitized images may be sent to the host computer 312, for example, via USB 2.0 high-speed interface. Video I/O connections may be made, for example, with 75Ω professional quality RG-59U coaxial cable and 75Ω BNC connectors and jacks.

Human machine interface (HMI) 314 allows an operator to interact with the hardware subsystem 310. In reference to FIG. 3C, operator interactions may proceed by way of a touch-screen display 344 (or other suitable input device or devices) and an emergency stop switch 342. Results generated in accordance with the present invention may be output-ted to a head mounted display (HMD) 348, system status LED display 346, and the touch-screen display 344. The operator interfaces with the system using the touch-screen display 344, for example, a sealed resistive touch-screen display. System status LED display 346 may be sealed and located on a bank next to the touch-screen to indicate proper functioning of the major components and act as a centrally-located status check. For example, the LEDs may be lit green for a functional component and blink red when the component has failed or not performing correctly.

HMD 348 is an output peripheral that places a micro display in front of the operator's eye in order for them to view data from the system. The data can include, for example, carcass images generated by the system. HMD 348 may be a rugged see-through prismatic display mounted on the visor of a hardhat or on safety goggles.

Transducer fixture 320 includes components for obtaining ultrasound images from the carcass sample. In one embodiment, the ultrasonic probe includes one or more pressure sensors located close to the transducer face, for example, one pressure sensor near the top of the transducer face and one pressure sensor near the bottom or an array of pressure sensors dispersed about the transducer face. The pressure sensor(s) are responsive to the transducer face contacting the carcass and provide a signal to the system that is used to record the pressure applied between the transducer face and the carcass. The recorded pressure data is associated with the images taken while at the respective pressure signal, and may be used for image screening (e.g., only images associated with pressure readings greater than a threshold value or falling within a specified range are analyzed) and/or for correction of output value (e.g., pressure data may be correlated to correction values that can be applied to the system results prior to outputting a final value). Pressure data may also be used to facilitate proper application of the transducer fixture to the carcass. For example, LEDs may be incorporated into the transducer fixture to implement a three-color light scheme whereby yellow indicates a standby status where the transducer is not on the carcass, green indicates that the transducer is on the carcass and the applied pressure is at a predetermined level or within a predetermined range (e.g., controlled or specified in software), and red indicates a fault situation such as when the applied pressure is too high for proper data acquisition, an insufficient number of valid data frames were acquired during a data acquisition time frame, and so forth.

Figure 3B:
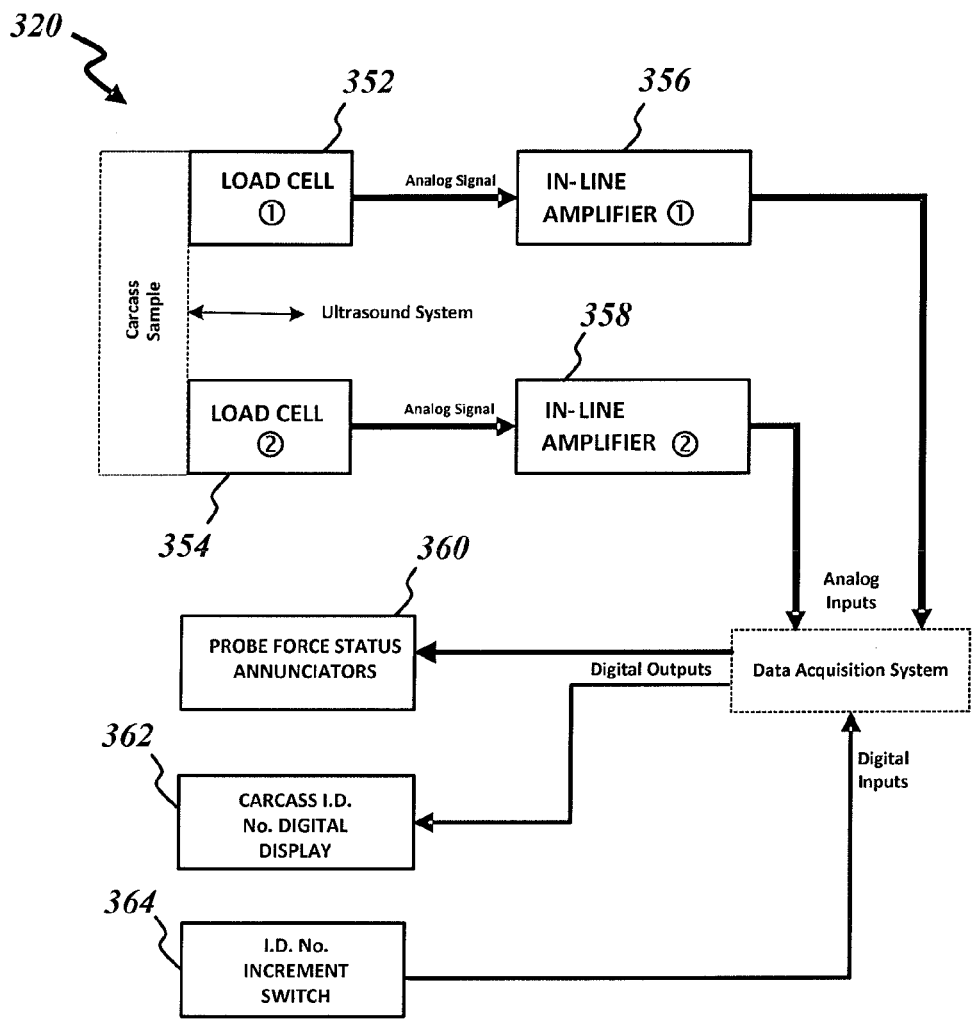
FIG. 3B shows a transducer fixture with pressure sensors, consistent with an example embodiment of the present invention.
Figure 3C:
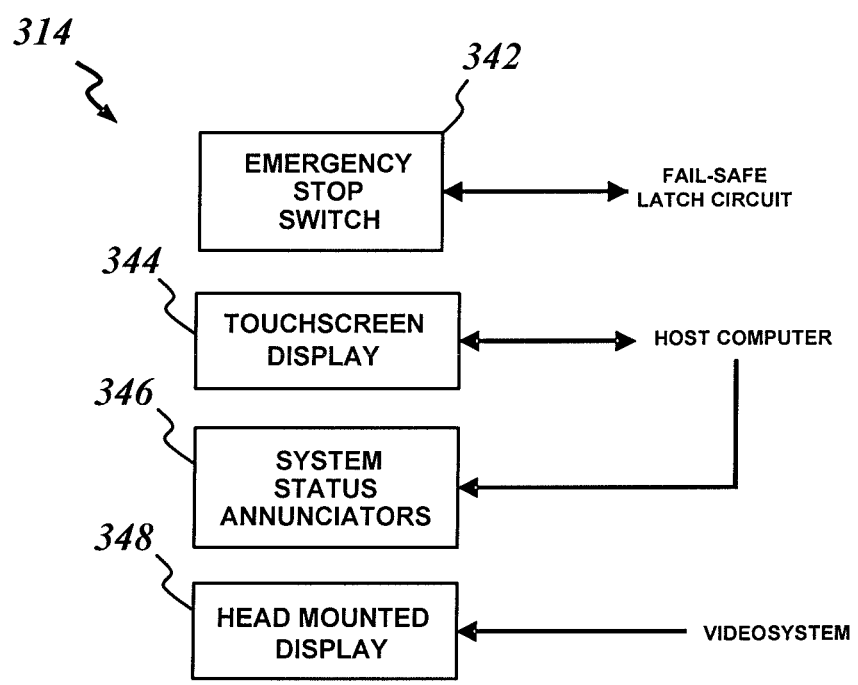
FIG. 3C shows various input and output interfaces, consistent with an example embodiment of the present invention.

Referring to FIG. 3B, load cells 352 and 354 of transducer fixture 320 sense the force applied between the ultrasound probe and the carcass skin. The load cells convert the force acting on it into a measurable electrical signal. Changes in the load result in a proportional change in the signal. Any suitable load cell may be used including, but not limited to, displacement sensors that sense variable capacitance between electrodes with respect to movement of the electrodes in response to an applied force.

In-line amplifiers 356 and 358 boost the strength of the load cell signals to a level usable by the data acquisition system. The amplifiers may be adjustable for each load cell, for example, to respond by outputting 0.5 Volts for every 1 pound of force applied.

Force data is sent through the data acquisition system to the capturing software and recorded with the images. Software may be used to decide if the ultrasonic probe transducer face is properly positioned and to provide feedback status information, for example, visually through probe force status LEDs 360.

In one embodiment of the present invention, digital display 362 is a washable, multi-digit LED readout mounted on the fixture, and may be used by the operator to associate a unique carcass identification number/name with a particular carcass. The current number of the sample is displayed until a new carcass is in position to be scanned. Automatic identification and data capture (AIDC) methods may be used, such as barcodes or RFID tags, to get data about samples and to enter that data automatically. A barcode may be imprinted on the sample so that the I.D. is machine-readable by an optical scanner. Passive radio-frequency identification (RFID) tags can be applied to or incorporated into an animal carcass for the purpose of identification using radio waves.

Working in conjunction with the carcass identification number digital display is an I.D. number increment switch 364 also mounted on the fixture 320. The switch 364 may be implemented as a button that the operator can press to manually advance I.D. The switch may be of the tactile feel feedback type that responds with a mechanical signal (typically a "snap" or "click") to indicate contact closure to the operator.

For purposes of scanning carcasses at a rapid rate by a human operator or by a robotic arm, the ultrasonic transducer fixture assembly may be supported by an overhead counterbalance and attached cable, and optionally provided with guides so the operator can quickly and properly align the transducer on the carcass.

Measurement of carcasses online in packing plants can be performed by human operators with the aid of measuring devices. However, humans tire and become distracted when doing monotonous activities. A robotic system offers repeatability and precision in application of the measuring device, even on moving carcasses. For example, a robotic system may employ a six-degrees-of-freedom arm guided by laser-vision sensors that scan each carcass to determine the precise positioning of the transducer and its fixture on the carcass. Variation in size and shape of individual carcasses can be accounted for so that linear measurement of subcutaneous fat and muscle measurements are made at the same relative anatomical position on every carcass. Various alternative location techniques can also be employed. For example, a human could mark a target location on the carcass (e.g., placing a visible mark on the carcass at the appropriate location). The automated arm can search for the marked location and properly place the ultrasound sensor based upon the marked location. This can be particularly useful for reducing the complexity of the positioning determination (e.g., simplifying automated machine vision and image processing) while allowing the actual placement and contacting of the ultrasound sensor to remain automated. Proximity and pressure sensors are used to insure that the transducer face is properly applied to the carcass for the capturing of images required for loin muscle tissue characterization for the prediction of percentage intramuscular fat.

Figure 3D:
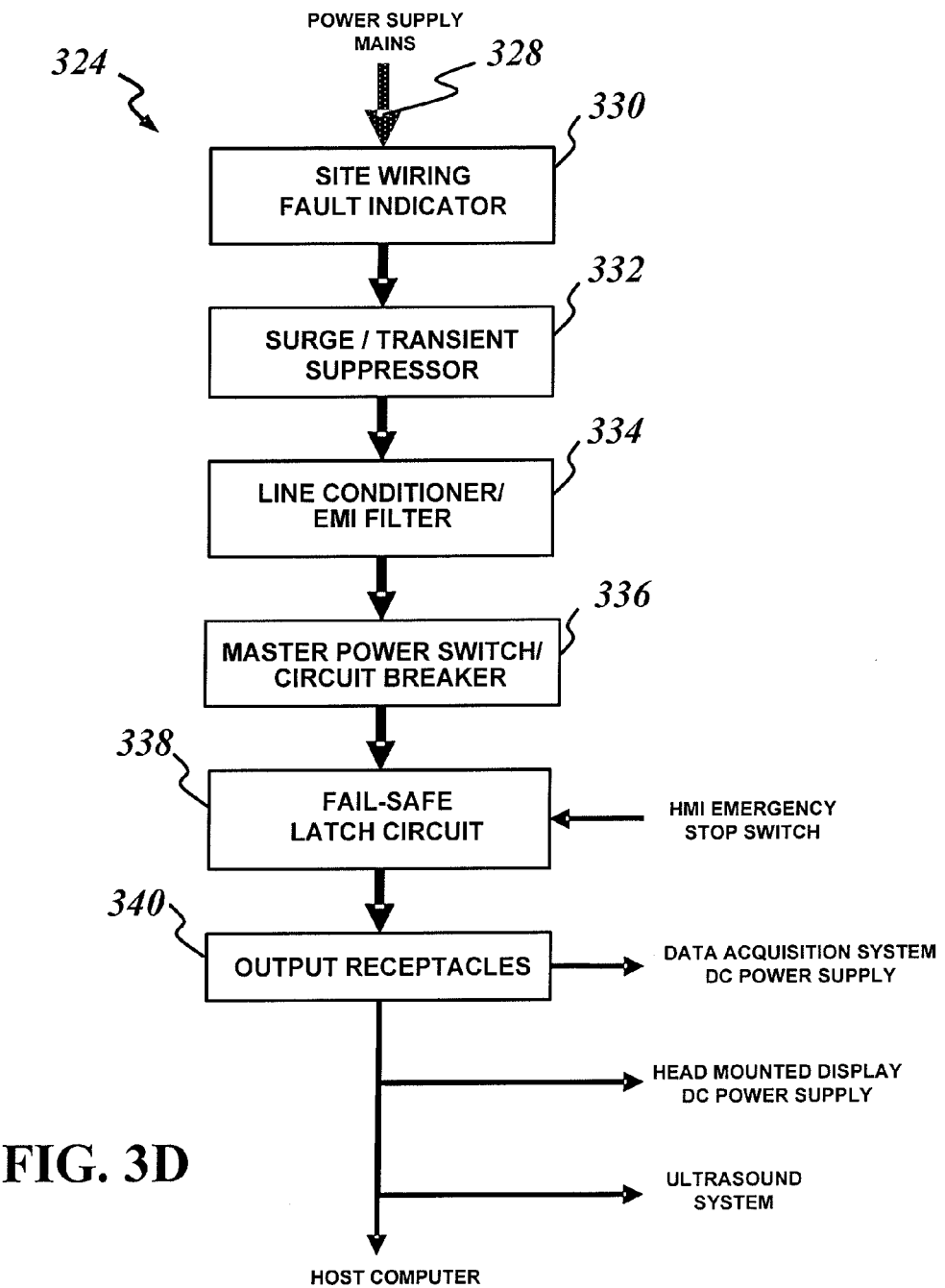
FIG. 3D shows various components of an exemplary power distribution unit 324, consistent with an example embodiment of the present invention.

In reference to FIG. 3D, various components of an exemplary PDU 324 are shown. In certain embodiments, PDU 324 powers all components by 120 Volts AC, 60 Hz, single phase, through a 2-pole, 3-wire rubber power cord 328 and a grounded straight blade or locking NEMA L5-15P watertight plug that connects to available power supply mains. Site wiring fault indicator 330 is an electrical unit that is illuminated if the power cord 328 is plugged into an improperly wired utility power outlet. Wiring faults detected include missing ground, hot-neutral polarity reversal, and overloaded neutral circuit. Surge/transient suppressor 332 protects equipment from over-voltages present on the AC power. The suppressor 332 operates by absorbing or blocking a surge from damaging the sensitive hardware components. Line conditioner/EMI filter 334 improves the "quality" of the power that is delivered to electrical load equipment by helping prevent voltage sags and surges from reaching the equipment, filtering small utility line fluctuations, and isolating equipment from large disturbances. The Electro-magnetic emissions EMI filter portion of PDU 324 attenuates conducted radio frequencies (RFI) between the line and the equipment. Master power switch and circuit breaker 336 may be implemented as a single sealed power switch on the main face of the PDU enclosure to perform normal power up and power down of the hardware subsystem. Fail-safe latch circuit 338 is used to latch all power circuits in a fail-safe manner. This circuit is a security measure used to shut off the hardware subsystem in an emergency situation in which it cannot be shut down in the usual manner, and may be operated in conjunction with an emergency-stop switch on the main face of the PDU enclosure. Output receptacles 340 are socket-type female electrical connectors that have slots or holes which accept the pins or blades of power plugs inserted into them and deliver electricity to the plugs. The receptacles may be conveniently located on a rear panel of the PDU, and may be hospital grade rated, such as 125 VAC 20 A NEMA 5-20R.

The electrical systems may be housed in a water-tight, corrosion-resistant enclosure suitable for sanitary wash-down environments. For example, the material of the enclosure structure and body may include 300 series stainless or better. The top of the unit may be sloped to reduce standing and pooling of water and cleaning solutions. The hardware unit may be mounted on resilient casters with locking mechanisms for ease of portability and stability when in use.

Accessibility for maintenance and routine service is available through access panels which are sealed with a non-porous continuous gasket capable of withstanding high pressure, high temperature jet stream wash-down. Heat Dissipation is managed in the unit by static ventilation (radiation/convection), whereby excess heat is transferred to the enclosure structure and body.

A specific embodiment of the present invention includes a pressure sensing fixture that mounts to the ultrasonic transducer and that can be disassembled for cleaning or repair as needed. In certain embodiments, the pressure sensing fixtures include two pressure load cells located and operated perpendicular to the face of the ultrasonic transducer (i.e., parallel to the direction of ultrasound wave propagation). In an exemplary arrangement, one load cell is located near the top end of the transducer (e.g., within 1 cm of the top) or near one end of the transducer and the second load cell is located near the bottom end of the transducer (e.g., within 1 cm of the bottom) or near the opposite end of the transducer. In another exemplary arrangement, the load cells are embedded into and are a part of the transducer lens and are in integral part of the transducer probe. These load cells indirectly measure the pressure being applied between the transducer lens face and the carcass as the transducer is applied to the carcass skin surface by the human operator or by a robotic arm.

Software algorithms or hardware are used to monitor the pressure readings from each load cell. The system associates the pressure readings with the video frames that were captured at the same time that the readings were acquired. In certain embodiments, live video streaming frames are used to calculate IMF content only when the load cell readings indicate that the transducer is being applied to the skin of the carcass within a specified range of pressure, for example, pressure higher than a minimum threshold, pressure lower than a maximum threshold, and/or pressure difference between the load cells is less than a maximum difference. The software may be used to control indicators such as two LEDs, one for each load cell. The processing software sends a code for turning the LED yellow if the pressure for that particular load cell has not reached a minimum level for acquiring images that allow proper tissue texture analysis. The processing software sends a code for turning the LED green when an appropriate pressure or pressure range is achieved. The processing software sends a code for turning the LED red if the pressure exceeds an acceptable pressure level. The frames captured outside the allowable pressure range may be rejected as not suitable for processing, although they may be saved for later analysis and system diagnostics purposes. Pressure level parameters within the processing software may be adjustable by service technicians and allow for maintaining proper calibration of the fixture and sensor configuration.

Figure 4A:
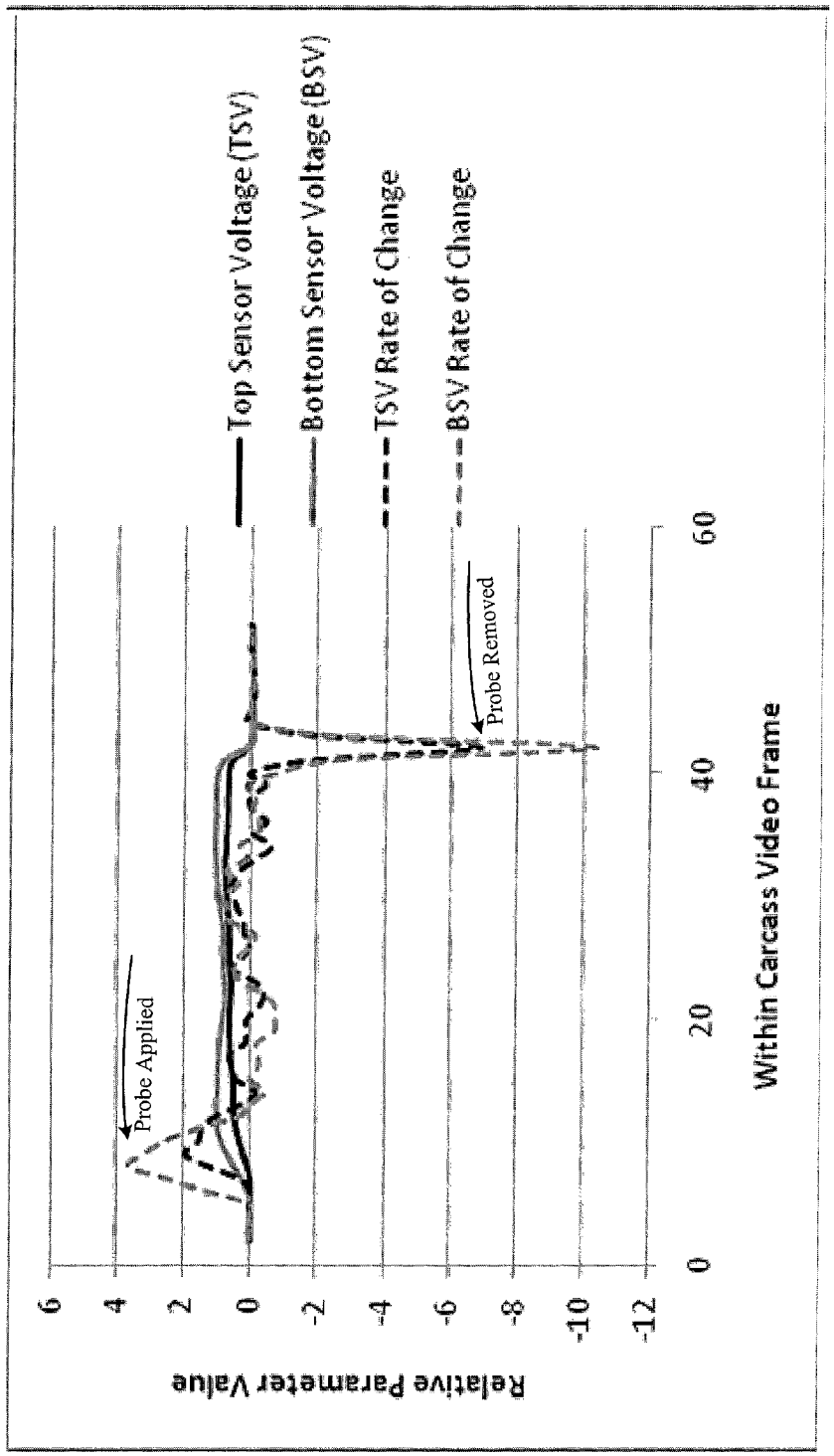
FIG. 4A illustrates the change in the voltage and voltage change rate for top and bottom pressure sensors within a carcass video frame, consistent with an example embodiment of the present invention.
Figure 4B:
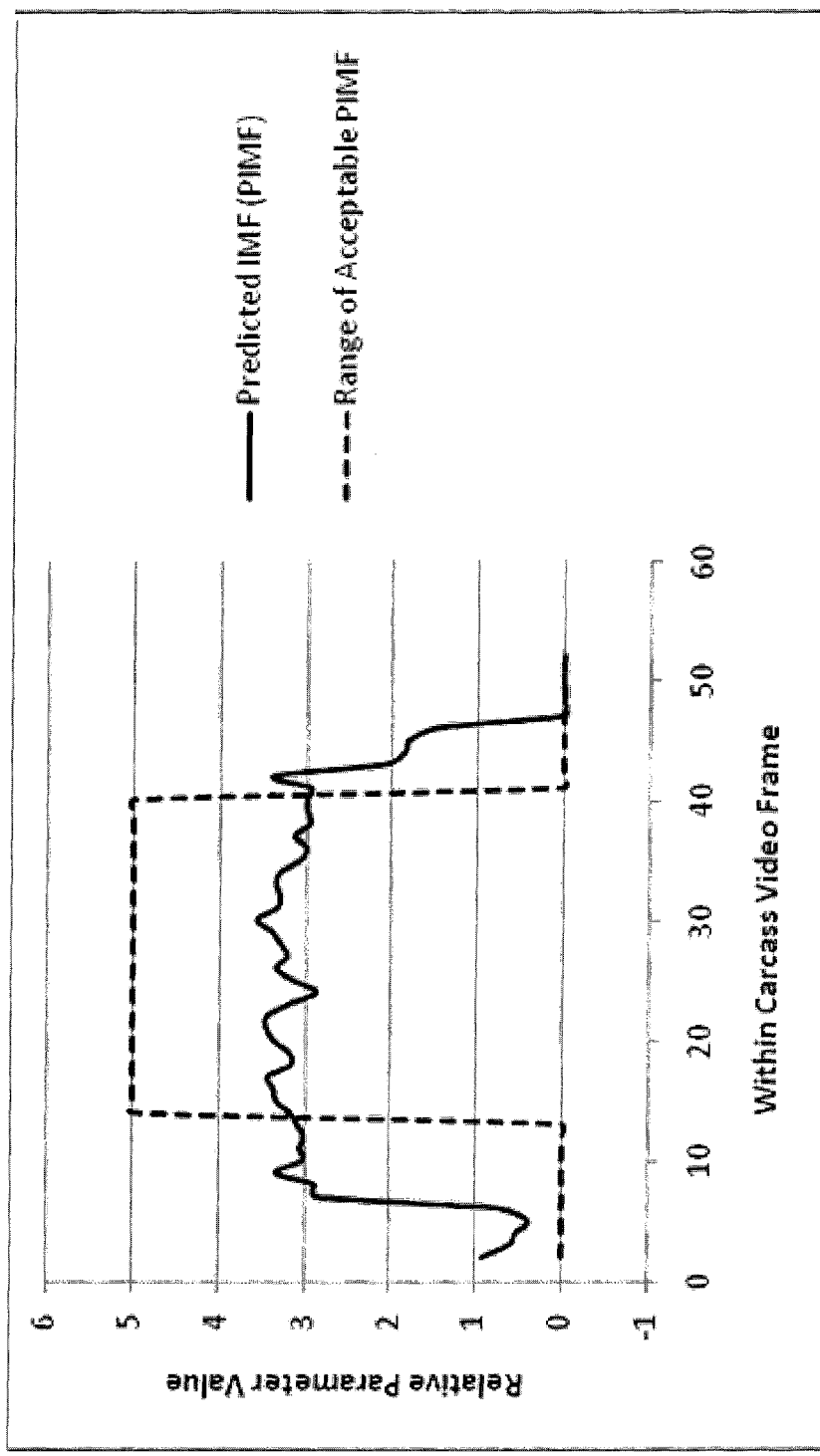
FIG. 4B illustrates the predicted IMF and the range of acceptable predicted IMF within a carcass video frame, consistent with an example embodiment of the present invention.
Figure 4C:
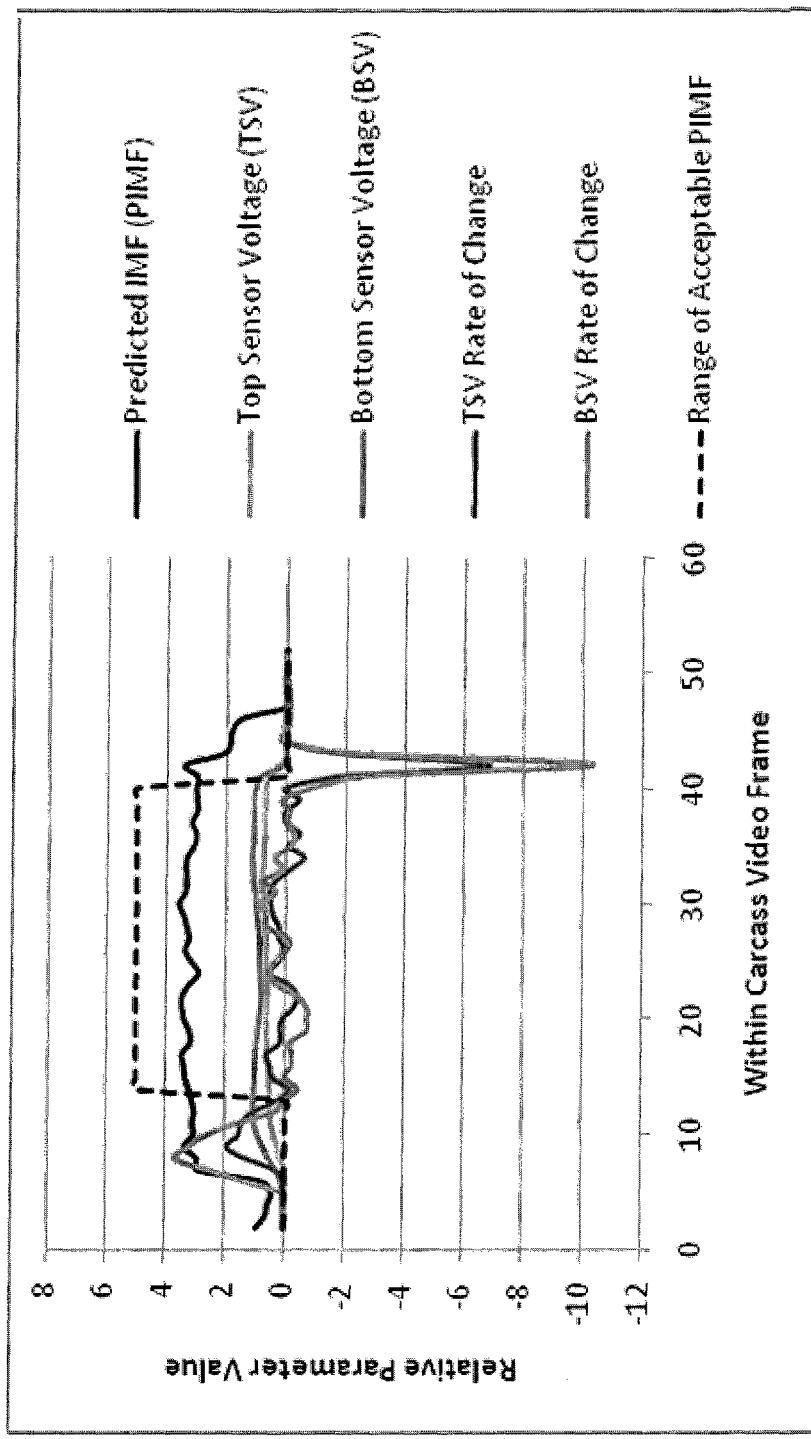
FIG. 4C illustrates the dependence of predicted IMF on the rate of change of voltages for top and bottom pressure sensors; consistent with an example embodiment of the present invention.

FIGS. 4A, 4B and 4C illustrate the dependence of predicted IMF on the pressure exerted by the transducer on the skin of the carcass. In FIG. 4A, the plot shows the voltage level being sent from the top pressure sensor and the bottom pressure sensor. The voltage level increases as pressure increases, e.g., as the transducer is being applied to the skin surface. The voltage level for each sensor increases to some steady state value as the operator seeks to stabilize the quality of the video stream of frames, with only minor change in value being seen. FIG. 4A also shows the rate of change of each sensor's voltage level. When the transducer is being applied to the skin of the carcass, and then again when the transducer is being removed, the voltage rates of change are at their peak values. An unexpected result is that both the voltage level and the rate of change of voltage are important parameters for the pressure filter. To provide high-levels of the accuracy in the tissue characterization, it can be important to verify that the image frames were captured with both the correct threshold range of pressure and a stabilized the rate of change that is also within a maximum threshold range. For example, if the current or previous frame sensor voltage is less than or equal to 0.49, then the current frame is ignored. Concurrently, if the difference between the current frame voltage and the previous frame voltage divided by 0.067 (the voltage rate change) is greater than 1.3, the current frame is ignored.

FIG. 4B shows the surprisingly accurate predicted IMF as it relates to the series of image frames corresponding to the pressure sensor values of FIG. 4A. As shown, the acceptable period for predicting IMF is surprisingly correlated with the parameters from the pressure sensor. FIG. 4C shows the overlay of the data from FIGS. 4A and 4B, further showing the surprising correlation between the pressure sensor input and the predictive accuracy in IMF measurement.

The hardware subsystem interfaces with and is controlled by the software system, which also screens and processes the captured ultrasound image. Each frame, or snap-shot, of the acquired ultrasound video signal is processed using selected sets or subsets of image processing algorithms to derive attributes of interest, such as IMF. Multiple such single frames are captured for each carcass to be evaluated.

Ultrasound video capturing and processing at a faster frame rate may be used advantageously for automated processing as well as certain applications such as chute-side analysis and carcass evaluation at a faster line speed (e.g., 1200 carcasses per hour). In accordance with certain embodiments, systems and methods of the present invention are used to capture and process ultrasound video imagery at variable frame rates (e.g., from 1 frame per second (fps) to 60 fps). Various processing modules or sets of processing modules can be selected and applied to the series of captured frames to extract tissue characteristics and attributes. Possible processing algorithms include frame editing, automatic image quality detection, fat thickness and muscle depth evaluation, and image texture processing.

In exemplary embodiments, the present invention may be used to first screen the acquired images for sufficient image quality. Next, image processing algorithms may be applied to automatically determine the fat layer boundaries, and then determine the rib locations (if visible on the image) and the top and bottom edge of the intercostales muscles. In accordance with certain embodiments, the present invention then determines one or more ROI of an image frame for further analysis, and selects and applies one or more image processing techniques in sequence or in parallel to the determined ROI. Automatic image processing and ROI determination can be used to reduce errors due to subjectivity of human intervention in interpretation of images. The further analyses are based on developed parameter values that may be used to generate an output value for a desired characteristic, such as IMF. Each of these steps, as well as the determination of parameter values for exemplary embodiments, is described in more detail below.

Video frames are continuously captured and processing of the captured images is implemented in response to the sensors on the transducer fixture indicating that a correct carcass skin to transducer lens face pressure range has been achieved. The pressure can be continuously monitored. Each frame for which a corresponding pressure measurement meets the pressure range criteria is evaluated for ultrasound penetration level through the first designated amount of skin (e.g., 0.69 mm for pork) as determined by histogram thresholding along the length of probe lens. Segments of the frame at the designated depth that exceed a set reflection intensity level (e.g., 179 pixel grey scale) are gated, and regions below these segments can be excluded from the development of texture parameters. Segments of the frame at the designated depth that exceed a set reflection intensity level (e.g., 200 pixel grey scale) are gated, and any region below these segments can be excluded from a determination of subcutaneous fat depth and muscle depth. Blurred frames as detected by a wavelet transformation algorithm may be excluded from further processing of tissue texture, but may be used for subcutaneous fat depth and muscle depth.

Frame editing procedures may optionally include frequent monitoring of the image contrast level by processing the grey scale bar on the ultrasound image, and monitoring for significant electromagnetic interference corrupting image frames.

A threshold step in image analysis is to screen acquired images so that acceptable images are used in the statistical analysis to develop an IMF regression model. For example, blurred images, images captured on carcasses where the structure of the skin has been significantly altered and will not allow the ultrasound to penetrate, and images captured during the ingress (placement) and egress (removal) of the probe to the skin surface may be discarded during the screening process. Blurred images may be detected by a wavelet blurring algorithm so that images with a blur factor greater than a specified level (e.g., 0.90 and greater) are defined as unacceptable and are not analyzed. Alternatively, the blur factor can be used to weight the importance of the images by, for example, decreasing the statistical importance of images as the blur factor increases. Images captured during placement of the probe, determined by the probe pressure sensors having not achieved a threshold of pressure value, can also be defined as unacceptable. Similarly, images captured during removal of the probe and associated with low probe pressure values may be discarded. Moreover, image frames that are captured when either (any) of the probe pressure sensors exceed a threshold amount, or when the difference between any two probe pressure sensors exceeds a threshold amount may be defined as unacceptable.

Other image screening techniques include evaluating the images for suitable portions to determine whether any suitable ROI exists in an image. For example, image regions where the average pixel value over the same horizontal line position exceeds a predetermined threshold grey scale (e.g., 150) may be flagged as unacceptable. After screening the images for regions of acceptability and unacceptability, those images that exhibit one or more independent ROI boxes of an appropriate size to be placed in the image are defined as acceptable; the others are defined as unacceptable. According to a specific embodiment of the present invention, the fat depth and loin depth of muscle tissue is determined. Fat depth and loin depth measurements are used in estimating fat free lean content in live and carcass food animals. Fat and loin depth measurements using ultrasound images offer a non-invasive method for this procedure. Automation of these depth measurements from ultrasound images can provide fast, efficient and consistent measurements compared to visual and manual tracing. Automation of depth measurements includes the automatic determination of the boundary positions for fat top, fat bottom, rib top, and the top and bottom interfaces of the intercostales muscles. These interfaces can be measured between all the rib pairs in longitudinal ultrasound images of live animals or carcass data (e.g., in swine, positioned between the $10^{th}$ and $13^{th}$ ribs). This offers the user the flexibility to select the preferred location for depth measurements. The following relationships can be defined:

Fat depth=Fat Bottom boundary−Fat top boundary

Loin depth=Rib top boundary−Fat bottom boundary, or

Loin depth=Intercostales muscles boundary−Fat bottom boundary.

The automation algorithm includes three subsections, each determining one of the above-mentioned boundary positions. Ultrasound image size (number of pixels along rows and columns) can vary depending on ultrasound scanner and frame grabber used for image capturing, and so the algorithm may be independent of image pixel size. The fat depth and muscle depth estimates are adjusted for the differences in ultrasound velocity in fat and muscle, respectively. A more detailed discussion of this procedure is given near the end of this document.

According to an embodiment, analysis of ultrasound images for tissue characterization purpose is facilitated by defining one or more "regions of interest" (ROI) within each image frame to be analyzed. The ROI selection process provides one or more representative areas of the full image for evaluation, and helps provide consistency among the representative areas evaluated from carcass to carcass.

After image screening, the selected image ROIs may be analyzed. ROI selection procedures are discussed in more detail later. An overview of various image analysis algorithms are discussed below.

Figure 5:
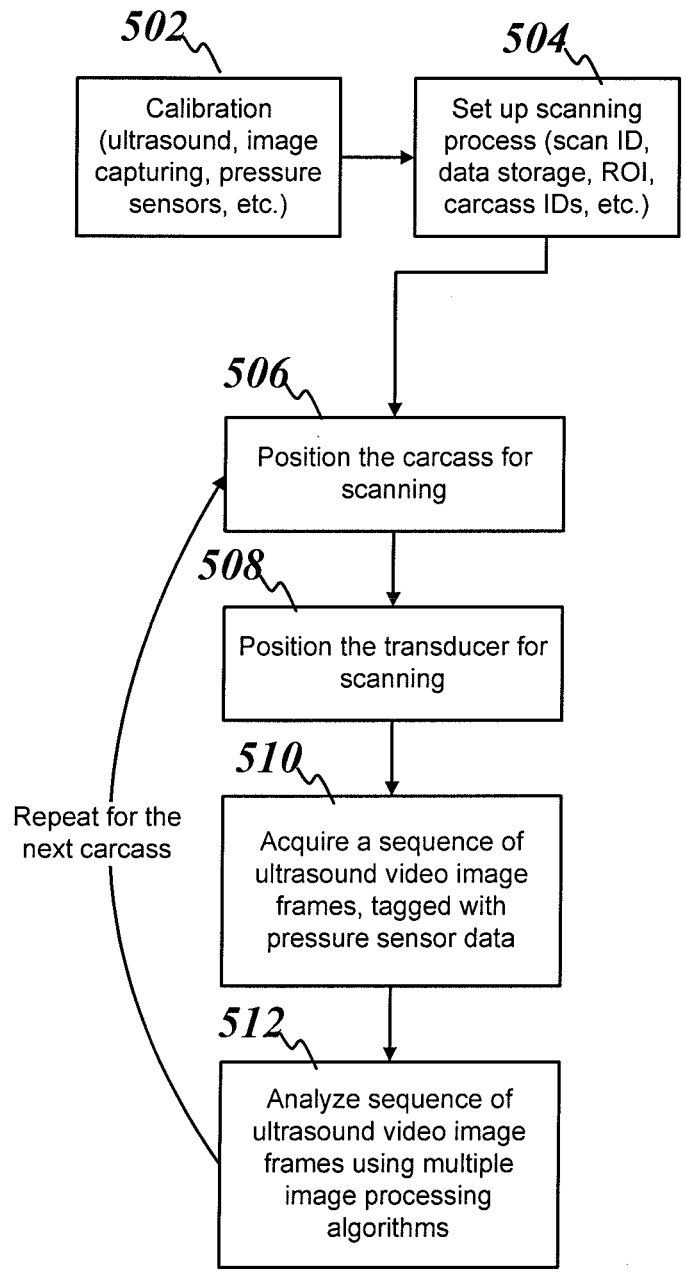
FIG. 5 presents an overall flow chart of an image acquisition procedure, consistent with an example embodiment of the present invention.
Figure 6:
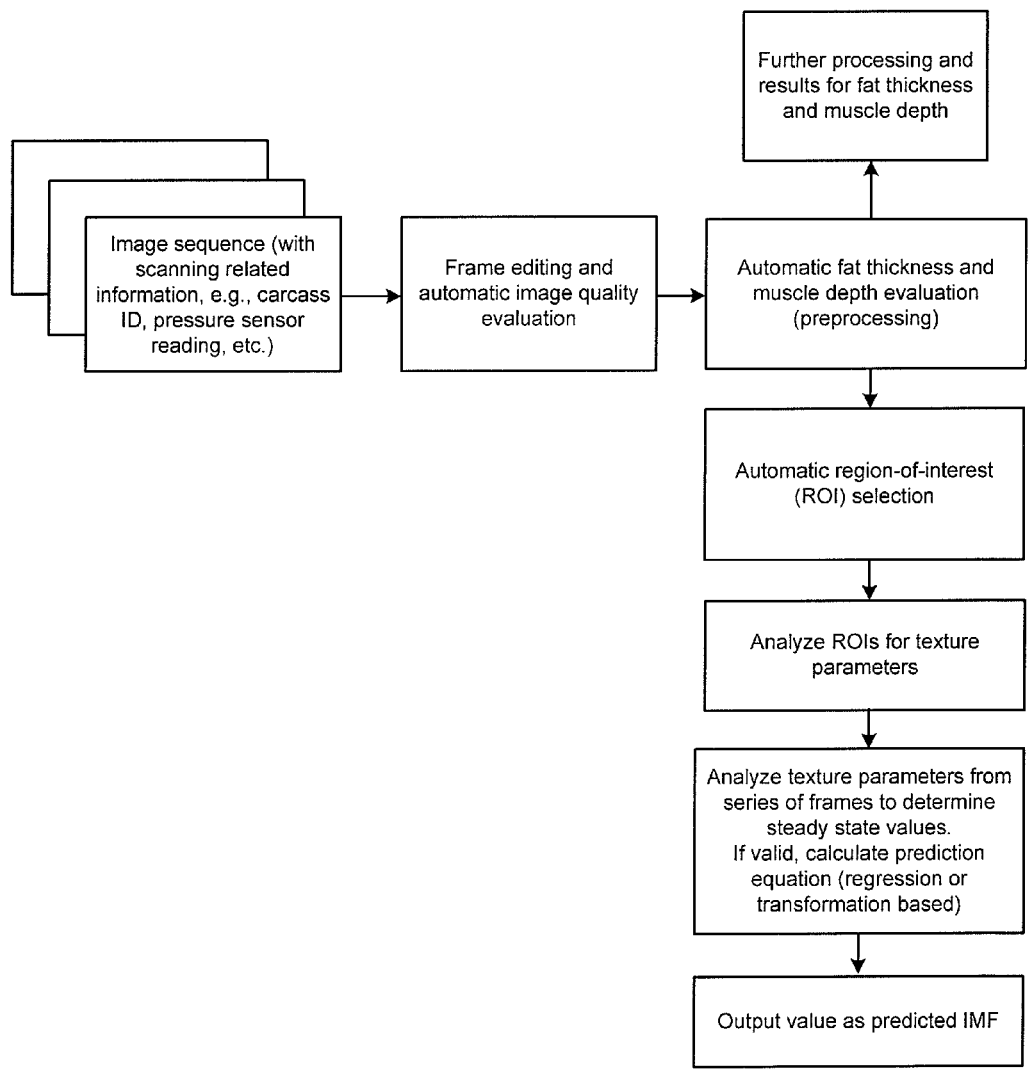
FIG. 6 illustrates an analysis procedure for image sequence, consistent with an example embodiment of the present invention.

Ultrasound images display a cross-section (in the plane of an ultrasound beam) of a tissue being scanned. The image displays variations in tissue density and acoustic impedance. Thus, various boundaries between different tissues (e.g., fat and muscle) are displayed. Additionally, each tissue has its own characteristic "ultrasound signature" that is displayed in the form of texture or speckle pattern on the image. This texture pattern also depends on the ultrasound transducer and scanner design and processing or the raw ultrasound data. In certain embodiments, the present invention utilizes image processing algorithms that can be used to determine the tissue characteristics in pork carcasses. The types of algorithms and overall flow chart of image frame processing are illustrated in FIGS. 5 through 7. For example, image processing based on two-dimensional Fourier transformations provides parameters highly correlated with the actual (chemical) IMF values. Such parameters may be combined in a prediction formula to estimate IMF in carcasses at a line speed.

Ultrasound calibration software algorithms may be used to set image capturing parameters to a given reference. Calibration works in combination with an ultrasound scanning device, the analog video signal from the scanner, and an image frame grabber. Calibration software may be used to automatically determine if the source of the video comes from any of five different ultrasound equipment types. Based on analysis of grey scale bars present in the images from these machines, calibration estimates actual signal voltage level and compares with a 1 volt reference. Understanding the signal strength differences between scanner brands as well as between scanners of the same brand may be used advantageously in the development of algorithms that can be used to predict % IMF from textural knowledge gleaned from ultrasound images for a variety of ultrasound scanner types.

Calibration also allows selection of the ROI within any given image to compare contrast histogram properties with a predetermined reference image (e.g., with the same ROI selected). The contrast and brightness differences are determined within each line of the image ROI and displayed visually, and overall percent differences are quantified and presented in the analysis window.

Calibration is also used for ultrasound scanner image normalization algorithms between different equipment types for texture parameters that relate to food animal and carcass tissue characteristics.

FIG. 5 presents an overall flow chart of an image acquisition procedure in accordance with certain embodiments. At step 502 the device can optionally be calibrated. Calibration can include testing and configuration of a number of different elements including, but not limited to, ultrasound, image capturing and pressure sensors. At step 504 the scanning process is set up. This can include scanning of carcass IDs, data storage of necessary information, ROI determinations and the like. At step 506 the carcass is positioned for scanning. The transducer is positioned (e.g., placed in contact with the carcass) for scanning at step 508. Step 510 involves the acquisition of a sequence of ultrasound video image frames. These images can be tagged with pressure sensor data, or otherwise filtered according to the pressure data. At step 512, the sequence of ultrasound video image frames are analyzed using multiple image processing algorithms. Steps 506-512 can then be repeated for subsequent carcasses as desired.

FIG. 6 illustrates an analysis procedure for an image sequence. The image sequence acquired from ultrasound video (e.g., captured in real-time) is first processed for frame editing to discard blank and poor quality frames. The fat thickness and muscle depth are calculated by applying image processing techniques (described in more detail below) followed by automatic ROI selection and further texture analysis using a selected set of processing and analysis algorithms depending on the parameters and the tissue characteristic of interest. The texture parameters may be further analyzed by various statistical techniques to select a desired list of parameters and develop coefficients and rules for IMF prediction.

Each image sequence can be identified with a carcass ID. Typical acquired images processed are of 512×486 pixels or 640×480 pixels, with the pixel values representing 256 shades of grey, although the described image texture analysis algorithms are applicable to any suitable image size and pixel range as well as various equipment settings. Specific results presented in this document are examples of specific equipment, settings and conditions, for example, using commercially available portable ultrasound scanners and typical equipment settings.

Figure 7A:
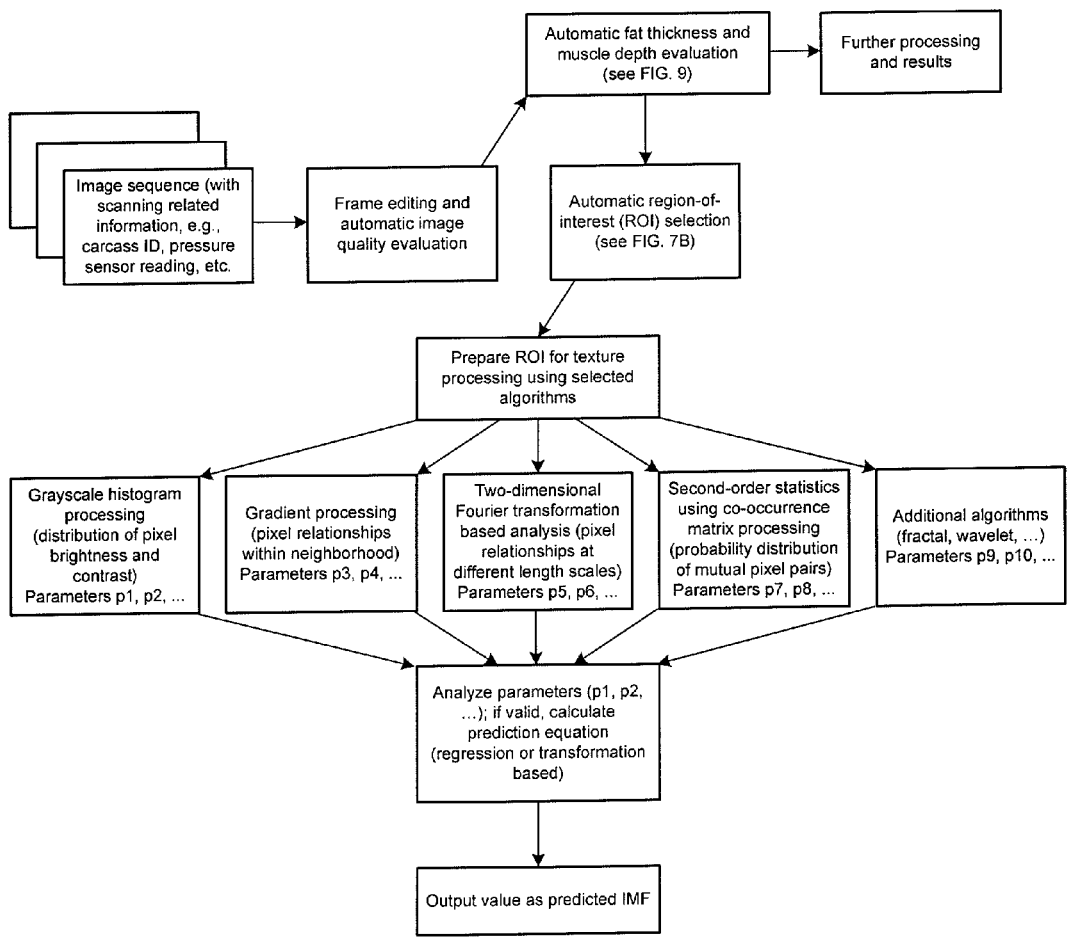
FIG. 7A illustrates the types of algorithms and overall flow chart of image frame processing steps used for an experimental study, consistent with an example embodiment of the present invention.

FIG. 7A illustrates the types of algorithms and overall flow chart of image frame processing steps used for the experimental study. The image sequence acquired from real-time ultrasound video is first processed for frame editing to discard blank and poor quality frames. The fat thickness and muscle depth (indicated in FIG. 7B and FIG. 9) are calculated by applying image processing techniques, which is followed by texture analysis. Texture parameters may be further analyzed by various statistical techniques to select a list of parameters and develop coefficients and rules for IMF prediction.

Figure 7B:
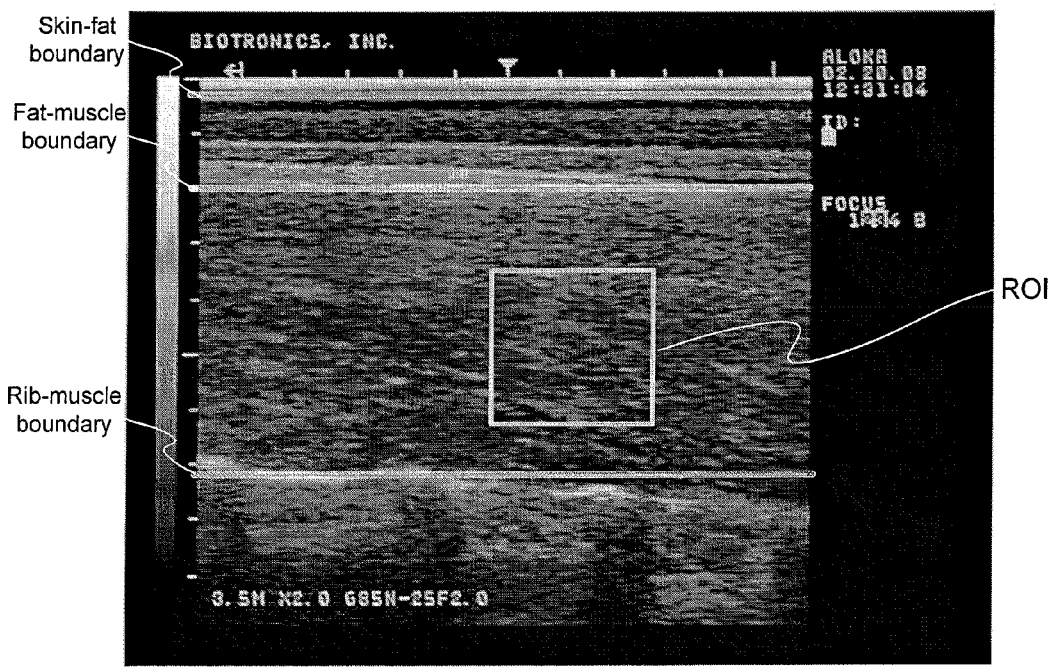
FIG. 7B illustrates fat thickness and muscle depth determinations, along with ROI selection, consistent with an example embodiment of the present invention.

Image analysis can be performed using computer-based image processing software or dedicated hardware, such as a programmable logic array. The image texture processing algorithms may be implemented as library modules. The image texture is analyzed by selecting and using regions-of-interest (ROIs) that are a subset of the overall image (e.g., 100×100 pixels or 80×80 pixels for the image sizes described above). The software may allow selection of additional ROI sizes, for example, to accommodate processing of smaller or larger muscles. Image processing then proceeds using one or more ROIs from each acquired image. An example selected image ROI is indicated in FIG. 7B.

Texture parameters are calculated from the ROIs based on the selection among several texture-processing algorithms, which include first-order statistical analyses such as histogram analysis, second-order statistics using co-occurrence matrix analysis, gradient processing, 2D Fourier transformation analysis, wavelet transformation analysis and fractal analysis, and so forth. Selection of parameters and texture-processing algorithms may depend on which parameters are best correlated to the tissue characteristics of interest. The degree of correlation along with coefficients used in the algorithms may be determined empirically, for example, by applying the texture-processing algorithms and comparing predicted results to a measurement of the tissue characteristics of interest.

Image ROI can be represented by a first-order probability distribution of image pixel amplitude (grey level). The shape of the image histogram characterizes the image. For example, histograms having wide amplitude distributions may indicate a high-contrast image. Histogram parameters such as mean, variance, skewness, kurtosis, mode, and percentile distribution provide information about image darkness, brightness, and contrast. In general, such image characteristics will depend on the equipment including its calibration and settings, as well as consistency of scanning procedures. As such, image characteristics calculated from first-order statistics may be better suited for providing information about the overall image quality than for providing parameters for quantifying the texture. In accordance with certain embodiments, acquired images may be screened based on the values of texture parameters from first-order grey level histogram, such parameters including skewness of the grey scale histogram (referred to herein as parameter p7), standard deviation of the grey scale histogram (referred to herein as parameter p16), and coefficient of variation of the grey scale histogram (referred to herein as parameter p17).

Image texture assessment may be performed by second-order-statistics, for example, based on co-occurrence matrix analysis. The co-occurrence matrix is a joint probability distribution of pairs of geometrically related image pixels. Co-occurrence parameters provide information on texture or speckle patterns in an image. This is based on the idea that the texture information in an image is contained in the overall spatial relationship which the grey tones in the image have to one another. A set of grey-tone spatial-dependence probability-distribution matrices may be computed from a given image block, and several textural features may be extracted from these matrices. These features contain information about image texture characteristics such as homogeneity, grey-tone linear dependencies, contrast, number and nature of boundaries present, and the complexity of the image. Grey level spatial-dependence probability distribution matrices are calculated at angles of 0, 45, 90, and 135 degrees. These matrices are then used to calculate several texture parameters such as contrast, sum entropy, difference variance, and correlation, as defined in image processing literature.

Fourier transformation techniques transform data into a form that provides information on the occurrence and frequency of repetitive features in an image. Fourier transformed images from a selected ROI may be used to determine the distribution of power at different frequencies. From such distributions, the rate of change in power from one frequency to another may be calculated using curve fitting algorithms and ratios of powers within different frequency ranges.

For a given image, let the ROI be of size N×N, and represented by I(x,y) which is function describing the grey level in x and y spatial coordinates. The Fourier transform F(u,v) is calculated according to the equation below, where u and v are spatial frequencies and $0 < u, v < N-1$.

$$F(u, v) = \frac{1}{N^2} \sum_{y=0}^{N-1} \sum_{x=0}^{N-1} I(x, y) e^{-j2\pi(xu+yv)/N},$$

The Fourier power spectrum may be computed as $Fp(u,v) = F(u,v) F^*(u,v) = |F(u,v)|^2$, where Fp is the sample power spectrum and * denotes the complex conjugate. The power spectrum is circularly shifted so that the center represents (0,0) frequency.

A coarse image texture shows high values of Fp concentrated near the origin, while a fine image texture shows a more spread out distribution of values. Similarly, a texture with edges or lines in a given direction $\theta$ has high values of Fp concentrated near $\theta+\pi/2$, while homogeneous textures have little or no directional concentration of Fp values.

From the Fourier power spectrum, two types of features are commonly calculated using annular and wedge sampling geometries. The ring shaped samples are calculated as:

$$F_R(r_1, r_2) = \sum_{\substack{r_1^2 \leq u^2+v^2 < r_2^2 \\ 0 < u,v < N-1}} F_p(u, v),$$

where r1 and r2 are inner and outer ring radii, respectively. The ring function is calculated for every radius of one pixel thickness (i.e., r2=r1+1). The function value for each ring is normalized by averaging over the number of pixels within the ring.

Typically, ultrasound image texture produces a ring function that can be approximated using an exponentially decaying function of the form $F_R(r)=ae^{-br}$, where r is the ring distance from the center. The coefficients a and b are used as descriptors of Fourier power distribution. The coefficient b can be considered as a measure of the ratio of high spatial frequency to low spatial frequency information. Additionally, the ring function values may be further characterized by ratios of power between two specific frequency bands. For example, a ratio of sums of ring values for radii less than 50% (normalized radius of half the width of the ROI Fourier transform) and radii more than 50% is calculated as:

$$FRP50 = \frac{\sum_{1 \leq r < N/2} F_R(r)}{\sum_{N/2 \leq r < N-1} F_R(r)},$$

where the Fourier ring value at radius 0 is ignored to avoid strong bias introduced by very high value at frequency (0,0) representing average grey value.

The Fourier wedge sampling geometry is defined as:

$$F_W(\theta_1, \theta_2) = \sum_{\substack{\theta_1 \leq \tan^{-1}(v/u) < \theta_2 \\ 0 < u,v < N-1}} F_p(u, v),$$

where $\theta 1$ and $\theta 2$ are the angles that define the wedge originating from (0,0). The Fourier wedge features such as mean and ratios may be calculated for the 15-degree wide wedge segments between zero and 180-degree angles.

Examples of Fourier transform-based texture parameters include the Fourier intensity coefficient of variation (standard deviation divided by mean), referred to herein as parameter p1; the ratio of Fourier powers within normalized frequency range of [0.01, 0.50] and [0.51, 1.00], referred to herein as parameter p2; and ratio of Fourier powers within normalized freq range of [0.01, 0.30] and [0.31, 1.00], referred to herein as parameter p3; and ratio of Fourier powers within normalized frequency range of [0.01, 0.10] and [0.11, 0.15], referred to herein as parameter p4.

Wavelet transformation can be used to analyze an image at different time and frequency scales. Discrete wavelet frame texture descriptors may be efficiently calculated using filterbank algorithms along with Haar wavelets with a low-pass filter and a corresponding high-pass filter.

Figure 8A:
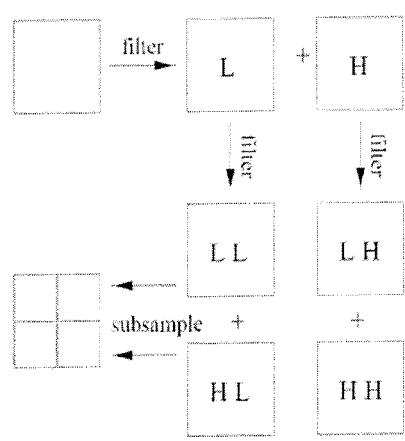
FIG. 8A indicates one level of wavelet decomposition in three steps of low and high pass filtering, consistent with an example embodiment of the present invention.
Figure 8B:
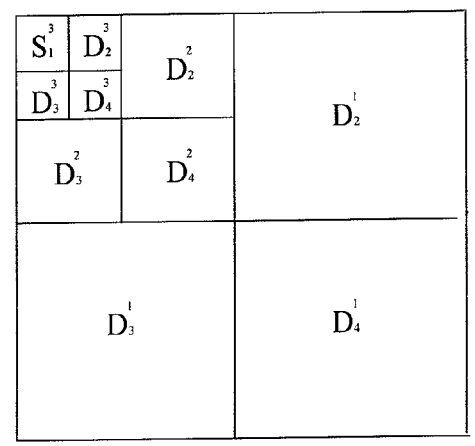
FIG. 8B shows a three level pyramidal structured wavelet decomposition of image data, consistent with an example embodiment of the present invention.

FIGS. 8A and 8B illustrate wavelet decomposition using low and high pass filtering. FIG. 8A indicates one level of wavelet decomposition in three steps of low and high pass filtering in the horizontal direction and vertical direction, and via subsampling. FIG. 8B shows a three-level pyramidal structured wavelet decomposition of image ROI. From three-level wavelet decomposition, energies in three high-pass sub-bands for each of the three levels may be calculated as texture parameters. For three-level decomposition, such methodology provides nine texture parameters, named W1 to W9 as follows: W1, W2, and W3 are the energy parameters in the three high-pass sub-bands for level-1 wavelet decomposition; W4, W5, and W6 are the energy parameters in the three high-pass sub-bands for level-2 wavelet decomposition; and W7, W8, and W9 are the energy parameters in the three high-pass sub-bands for level-3 wavelet decomposition.

The usefulness of image features or parameters derived therefrom depends on the information content and how sensitive and specific the feature is to the differentiation or characterization problem of interest. In accordance with certain embodiments, selecting and using sets or subsets of texture parameters based on ultrasonic images is used in tissue characterization and classification. In exemplary embodiments, statistical methods are used to select a set of parameters that show significant correlation with chemical IMF and provide robust predictive capability. In addition, statistical methods may be used to screen and select acquired images that are most likely to produce reliable results.

As discussed, ultrasound-based systems in accordance with certain embodiments of the present invention are used for live or carcass animal evaluations utilizing multiple-frame image analysis. Each acquired ultrasound image frame is screened sequentially, and ROI of the images are selected and processed using image processing algorithms to derive attributes of interest. Such ultrasound video capturing and processing may be performed at rates that allow automated processing as well as chute-side analysis and carcass evaluation in real time, potentially allowing for faster line speeds (e.g. 1200 carcasses per hour or more).

As described, scanning systems include an ultrasound scanner that produces ultrasound video images and pressure sensor reading inputs to a processing computer that stores the incoming information in real-time and at line speeds. As with any multi-component system, the slowest component determines the final rate of the system. Certain embodiments of the present invention may be used to capture sufficient numbers of ultrasonic video images at line speeds, and automatically processes the images using frame editing, image quality detection, fat thickness and muscle depth evaluation, and image texture analysis to extract tissue characteristics and attributes, such as IMF.

In exemplary embodiments, the present invention may be implemented as an online pork loin IMF prediction system, for example, usable by a packing plant to sort pork carcasses for processing, product marketing, and paying pork producers for their harvested pigs. Systems and methods of the present invention may be employed on hot pork or beef carcasses (hot, meaning within 45 minutes postmortem), and where IMF (or other tissue characteristic) prediction is desired to be performed real-time so that the data can be interfaced directly with other carcass data and before the carcass leaves the hot carcass processing part in the harvesting plant.

Scanning of carcasses moving on a transport system within a packing plant for purposes of predicting IMF level within an individual carcass presents conditions that may be addressed using systems and methods in accordance with certain embodiments of the present invention. For example, in typical packing plant processing environments, carcasses are moving by the scanning station at the rate of approximately 1,200 carcasses per hour. In other words, there is less than 4 seconds of time available to accurately apply an ultrasound probe on the skin of the carcass, capture the imagery, perform the analysis to predict IMF (or other characteristics), interface the data with other carcass data such as animal identification, remove the probe from the skin of the animal and prepare to repeat the process for the next in line carcass.

In systems and methods of the present invention, an operator (human, automated, or combination) positions the ultrasonic probe on the skin of the carcass, and the remaining processes follow automatically, including the capture of carcass identification and live video image frames.

In exemplary pork loin processing embodiments, the operator positions and maintains the ultrasound transducer (probe) fixture so that the probe is vertically aligned with and parallel to the spin or midline of the carcass, between 2 and 7 cm lateral to the midline, and on either side of the carcass. In typical packing plant environments, the carcass is vertically suspended on a trolley system. The top portion of the transducer face may be positioned so that the ultrasound image will include the last 3 to 4 ribs of the carcass.

The procedure for scanning carcasses involves a steady stream of video frames being captured and stored for each test carcass. For an exemplary ultrasound scanner and probe such as manufactured by ESAOTE Pie Medical and available under model number Aquila Vet ultrasound scanner model number 401611 ASP 3.5 Mhz probe, the nominal frame rate is 26 fps. For an exemplary ultrasound scanner and probe such as manufactured by Aloka and available under model number SSD 500V ultrasound scanner and UST 5011 3.5 Mhz probe, the nominal frame rate is 11 fps with the normal focal depth settings of focal zones 2 and 3 being enabled. As will be appreciated, any suitable scanning settings may be used, taking into consideration that direct data comparison between carcasses will be more readily obtained when the selected equipment settings are kept constant (image texture parameters are influenced by pixel grey scale level, which can vary significantly with different settings). Exemplary settings for the Aloka SSD 500V include a magnification of X2.0, overall gain of 85, near gain set at −25, far gain set at 2.0, frame correlation set to auto, contrast set to 4, and automatic gain control set to 1.

After various selected image screening techniques are applied, the acceptable images for a given carcass are used in the prediction of IMF level. During experimentation, it has been observed that screening such as described above generally results in at least 2 acceptable images and as many as 27 acceptable images during a 30 frames per second image acquisition scan, with the average number of acceptable frames per carcass found to be 12.6±4.1 out of a total of 7,668 frames evaluated from 700 carcasses.

As noted above, it may be useful to define an acceptable image as one that allows a minimum of two non-overlapping acceptable ROIs to be placed and evaluated. In exemplary embodiments, the ROI are positioned within the longissimus dorsi muscle, with the ROI size being selected to increase the texture area to be processed so long as the ROI does not undesirably include interface echoes, rib tops, subcutaneous fat, intercostales muscles or fat interfaces.

The amount of time varies that a probe is positioned on a carcass to capture live ultrasound video. Also, the number of acceptable frames varies from carcass to carcass. It has been observed that the IMF prediction model is most accurate using images captured when the probe is effectively positioned on the carcass (defined by acceptable images being captured) for about 1 or more seconds.

To develop a tissue evaluation model that produces a predictive value for a tissue characteristic of interest from analysis of captured ultrasonic video frames, a statistical analysis can be applied to determine the confidence level associated with various parameters. Prediction of tissue characteristics from image data, and particularly ultrasound image data to predict percentage IMF, was facilitated by a number of discoveries related to the specific statistical analysis of the image parameters and their ability to accurately model the tissue characteristics. Such statistical analysis then facilitates the selection of parameters and processing algorithms. In certain embodiments, the present invention combines descriptive tissue characterizing texture parameters into a regression model that is predictive of percentage IMF, and that is accurate according to a set of $R^2$, root mean square error (RMSE) statistical, bias and correlation standards. The following description provides an experimental process and related data consistent with an example of performing such characterization.

As an initial step, the acquired images are screened for image quality so that the texture parameters are calculated for a set of images that conform to editing standards. A natural logarithmic transformation to the base e of the dependent variable may be used for food animal IMF prediction models in order for the residual errors to conform to a normal distribution assumption. Regression models are optimized for hardware configurations, environment and being either live animal or carcass. One possible regression model is of the form:

$$\text{Predicted \% IMF} = -0.086614860 + mz1*1.297367893 - mz3*0.086056279 - mz4*1.25833393 - mz7*1.871074428, \text{ where}$$

$$mz1 = 0.5*mp1 + 0.5*mq1,$$

$$mz3=0.5*mp3+0.5*mq3,$$

$$mz4=0.5*mp4+0.5*mq4,$$

$$mz7=0.5*mp7+0.5*mq7,$$

and where mpi and mqj are individual texture parameter values from ROIi and ROIj within each carcass image, and where final predicted percentage intramuscular fat is equal to e (irrational constant) raised to the power of the predicted percentage intramuscular fat if a natural logarithmic transformation is used.

In certain embodiments, methods of analysis according to the present invention assume a linear model with dependent variable, y, as the chemical fat data and independent variables as a list of possible texture parameters that are determined from within the texture of each defined ROI within each frame. The y variable is defined as the percentage of total chemically extractable fat from a loin muscle tissue sample.

Candidate regression models are identified with PROC STEPWISE (SAS Institute Inc., Cary, N.C., USA) and PROC RSQUARE (SAS Institute Inc., Cary, N.C., USA) for further study using maximum $R^2$ and Mallows' $C_p$ statistic. Outlier texture parameters within a carcass are identified with PROC ROBUSTREG (SAS Institute Inc., Cary, N.C., USA) and those carcass image frames are eliminated from further consideration. The model development may be refined with PROC GLM (SAS Institute Inc., Cary, N.C., USA). Analysis models where the level of significance for each independent parameter is <0.0001 may be selected for final model validation. It is useful to consider both first and second order polynomial models, and using accuracy statistics such as model $R^2$, RMSE, and distribution of residuals. Once a final model is selected, the dependent variable is regressed on the predicted IMF level for all carcasses within the model development and validation data sets to determine the prediction model root mean square error (RMSE). The model is of the general form:

$$y_i = b_0 + b_1 * p_{i1} + b_2 * p_{i2} + \ldots + b_{10} * p_{i10} + e_i,$$

where, $y_i$=% IMF for the $i^{th}$ carcass loin muscle sample, and where the final predicted percentage % IMF is equal to $y_i$; $p_{ij}$=$j^{th}$ texture parameter values for the $i^{th}$ carcass ($1^{st}$ and $2^{nd}$ order); and $e_i$=random residual error for the $i^{th}$ carcass.

The assumption that the residuals, $e_i$, are normally distributed is not necessary for estimation of the regression parameters and partitioning of the total variation. However, normality may be established for tests of significance and construction of confidence interval estimates of the parameters. Transformation of the dependent variable to a form that is more nearly normally distributed is the usual recourse to non-normality. Heterogeneous variance, as non-normality, may generally be expected, and may be handled using transformation of the dependent variable and weighted least squares. It has been observed that a natural logarithmic transformation of the dependent variable, chemical IMF, is suitable to reduce heterogeneous variance.

It was observed that using two or more ROIs in each analyzed image improved model $R^2$ approximately 5% over using a single ROI per image.

Development of an IMF prediction model that relies upon the processing of ultrasound imagery includes developing a database of images captured from a large number of individually identified pork carcasses and from carcasses that exhibit considerable variation in terms of their IMF level. For example, muscle tissue samples can be taken from each loin scanned and from the direct vicinity of the ultrasound scanning and subjected to a wet laboratory procedure that can be used to objectively and quantitatively determine the actual total chemical fat in the tissue sample. Other comparative data that may be collected from each loin scanned includes marbling score, which is a subjective and visually determined numerical score for IMF. Once the database is developed (images, chemical intramuscular fat readings, and marbling score) for the individual carcasses, a statistical analysis is performed to identify image textural parameters and their respective and proportional influence on the level of IMF within the loin muscle of an individual carcass.

At the outset of the statistical analysis, an in depth review of each frame capture for each carcass is made and a determination is made as to the quality of the image. Unacceptable images are so classified in the database and excluded from further analysis. A subset of the database is selected for the development of alternative prediction models, and then promising candidate models are tested on a different subset for purposes of validation. The final product is a regression model that can be used for prediction of IMF on other carcasses that employ the same equipment and scanning procedures.

This approach was validated using a total of nine plant scanning sessions in which approximately 80 carcasses were scanned during each session. At the end of the data collection period, a total of 671 carcasses had been scanned that included harvest facility, scanning date, images, marbling score and chemical fat data. The data is summarized in Table 1. Groups 2-7 were used in the development of what is referred to herein as the IMF prediction model, and groups 1, 8, and 9 were used as validation groups.

TABLE 1

| Harvest Date | Scanning Group | No. Carcass Observations after Edits | Model Development | Model Validation | Outliers Detected |
|---|---|---|---|---|---|
| A | 1 | 75 |  | Yes | 0 |
| B | 2 | 76 | Yes |  | 0 |
| C | 3 | 21 | Yes |  | 0 |
| D | 4 | 79 | Yes |  | 1 |
| E | 5 | 79 | Yes |  | 0 |
| F | 6 | 89 | Yes |  | 0 |
| G | 7 | 73 | Yes |  | 2 |
| H | 8 | 74 |  | Yes | 1 |
| I | 9 | 73 |  | Yes | 3 |

The preliminary analysis from various texture parameters may be performed by calculating correlation and cross-correlation coefficients and their significance levels (p values). Table 2 presents an example of such results for parameters that have been observed to show significant correlation with chemical IMF values, using 639 carcasses. In the results below, the determined IMF is the intramuscular fat from the loin eye samples as determined by chemical extraction. The parameters presented in the table are defined as follows:

p1=Fourier intensity coefficient of variation (standard deviation divided by mean);

p2=Ratio of Fourier powers within normalized freq range of [0.01, 0.50] and [0.51, 1.00];

p3=Ratio of Fourier powers within normalized freq range of [0.01, 0.30] and [0.31, 1.00];

p7=ROI pixel grey scale histogram skewness;

p16=ROI pixel grey scale histogram standard deviation;

p17=ROI pixel grey scale histogram coefficient of variation; and

IMF=intramuscular fat from the loin eye samples as determined by chemical extraction.

TABLE 2

|     | IMF   | p1    | p2    | p3     | p7     | p16  | p17  |
|-----|-------|-------|-------|--------|--------|------|------|
| IMF | 1.00  |       |       |        |        |      |      |
| p1  | 0.34  | 1.00  |       |        |        |      |      |
| p2  | 0.21  | 0.87  | 1.00  |        |        |      |      |
| p3  | 0.19  | 0.94  | 0.94  | 1.00   |        |      |      |
| p7  | −0.35 | −0.52 | −0.43 | −0.39  | 1.00   |      |      |
| p16 | −0.26 | −0.22 | 0.16  | −0.05[a] | −0.06[b] | 1.00 |      |
| p17 | −0.41 | −0.93 | −0.74 | −0.80  | 0.58   | 0.36 | 1.00 |

[a] $p = 0.2356$,
[b] $p = 0.1577$,
all others have p value < 0.0001

Table 3 presents correlation results for wavelet and Fourier parameters using ultrasound scans from 69 live pigs and chemical IMF. The wavelet based parameters presented in the table are:

W1, W2, W3=Energy in the three high-pass sub-bands for level-1 wavelet decomposition;

W4, W5, W6=Energy in the three high-pass sub-bands for level-2 wavelet decomposition; and W7, W8=Energy in the upper two high-pass sub-bands for level-3 wavelet decomposition.

TABLE 3

|     | IMF   | P1   | P2   | P3   | P4    | W1   | W2   | W3   | W4   | W5   | W6   | W7   | W8   |
|-----|-------|------|------|------|-------|------|------|------|------|------|------|------|------|
| IMF | 1.00  |      |      |      |       |      |      |      |      |      |      |      |      |
| P1  | 0.38  | 1.00 |      |      |       |      |      |      |      |      |      |      |      |
| P2  | 0.22  | 0.94 | 1.00 |      |       |      |      |      |      |      |      |      |      |
| P3  | 0.28  | 0.97 | 0.96 | 1.00 |       |      |      |      |      |      |      |      |      |
| P4  | 0.47  | 0.95 | 0.83 | 0.89 | 1.00  |      |      |      |      |      |      |      |      |
| W1  | −0.11 | 0.16 | 0.30 | 0.13 | 0.09  | 1.00 |      |      |      |      |      |      |      |
| W2  | −0.19 | 0.07 | 0.22 | 0.06 | −0.01 | 0.90 | 1.00 |      |      |      |      |      |      |
| W3  | −0.12 | 0.17 | 0.33 | 0.16 | 0.08  | 0.97 | 0.92 | 1.00 |      |      |      |      |      |
| W4  | −0.20 | 0.07 | 0.24 | 0.07 | −0.03 | 0.96 | 0.94 | 0.98 | 1.00 |      |      |      |      |
| W5  | −0.23 | 0.11 | 0.25 | 0.13 | 0.01  | 0.67 | 0.90 | 0.75 | 0.77 | 1.00 |      |      |      |
| W6  | −0.11 | 0.17 | 0.32 | 0.17 | 0.07  | 0.86 | 0.90 | 0.95 | 0.92 | 0.82 | 1.00 |      |      |
| W7  | −0.17 | 0.10 | 0.24 | 0.11 | 0.00  | 0.73 | 0.83 | 0.83 | 0.85 | 0.82 | 0.93 | 1.00 |      |
| W8  | −0.23 | 0.14 | 0.25 | 0.17 | 0.05  | 0.46 | 0.70 | 0.56 | 0.56 | 0.91 | 0.67 | 0.71 | 1.00 |

The final regression parameters determined for the IMF prediction model developed in accordance with the present invention for pork loin are presented in Table 4.

TABLE 4

| Texture Parameter | Regression Coefficient Estimate | Probability > \|t\| Statistic |
|---|---|---|
| $b_0$, intercept | 1.442867943 | <.0001 |
| $b_1$ | .107983285 | <.0001 |
| $b_2$ | .002812736 | <.0001 |
| $b_3$ | −.030314266 | <.0001 |
| $b_7$ | −.440864806 | <.0001 |
| $b_{16}$ | −.045328050 | <.0001 |
| $b_{17}$ | na | |

Accordingly, aspects of the present invention provide an unexpectedly accurate prediction of relative IMF content using an automated image-processing system. The predictive ability is further underscored by the correlation between the prediction and chemical-based IMF measurements. Chemical-based IMF measurements provide an objective measurement that does not rely upon subjective visual measurements. Thus, the ability to use imaging technology to accurately predict a chemical measurement allows for the use of noninvasive (e.g., ultrasound) imaging technology in fully-automated processing systems.

In various embodiments, determining fat depth and loin depth can be important for predicting fat-free lean in swine carcasses, and may form an initial step in analyses performed in accordance with the present invention. There are different types of methods for fat and depth determination, some of which include manual measurements that include 10th rib backfat and loin area; using an insertable optical probe; cross-sectional scanning; and ultrasonic scanning. While manual methods have been observed to be relatively precise, accurate measurements require highly trained technicians and the process is time-consuming and labor intensive. In accordance with aspects of the present invention, fat depth and muscle depth determinations can be made from longitudinal scans of ultrasound images, and such processes may be automated.

Figure 9:
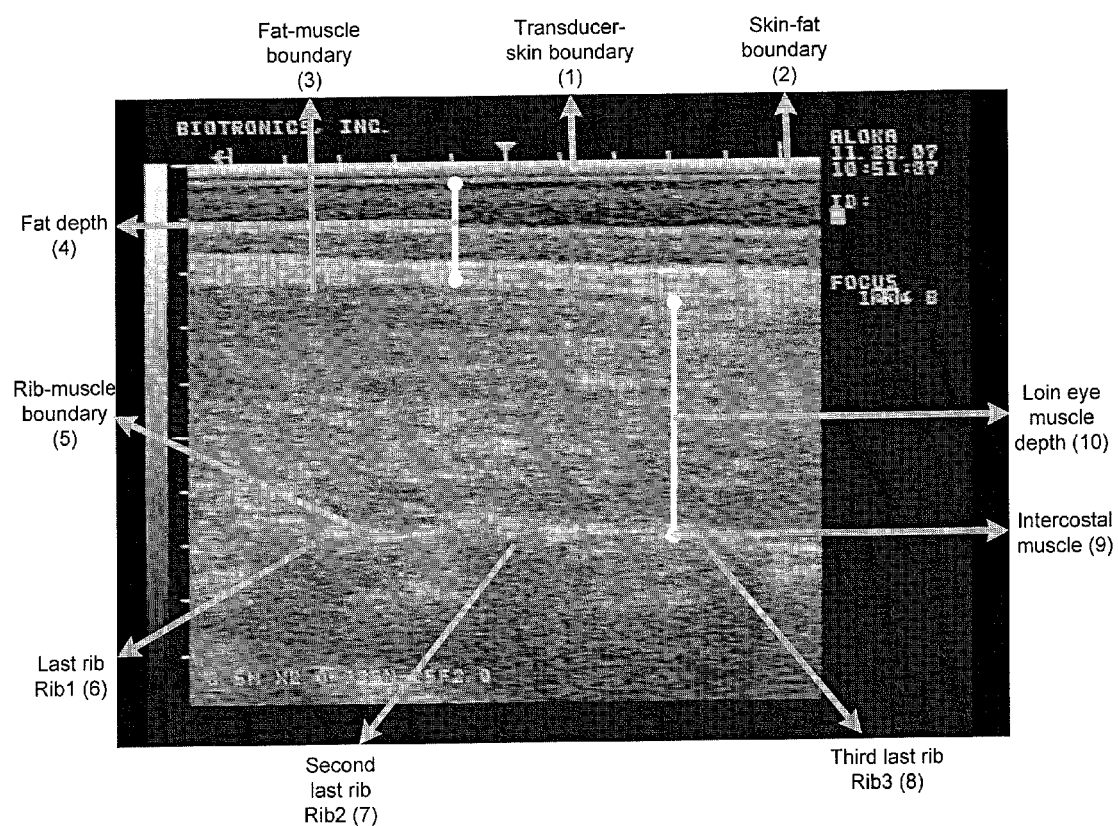
FIG. 9 is an ultrasound image of a swine carcass loin eye muscle, consistent with an example embodiment of the present invention

FIG. 9 is an ultrasound image of a swine carcass loin eye muscle, captured using an Aloka SSD 500V ultrasound scanner, a 12 cm linear transducer of 3.5 MHz and a Sensoray 2255S frame grabber. It is a longitudinal image of a swine carcass positioned over the last 3 to 4 ribs. The top-most light-grey band is the transducer skin boundary 1. Below this is very thin light grey line which is the skin-fat boundary 2. There are further light-grey bands that correspond to three fat layers and fat-muscle layer boundary 3. The last three ribs, 6, 7, and 8, respectively, are clearly seen in the lower half of image as three vertical columns with the intercostales muscles 9 holding the ribs. The muscle above these ribs is the longissimus dorsi muscle. The boundary between the loin eye muscle and the ribs is the rib-muscle boundary 5.

A process for determining the fat depth 4 and loin eye muscle depth 10 may be automated for swine carcass data in a real time live-streaming scanning system. The fat depth 4 is the difference between the two boundary positions, skin-fat 2 and fat-muscle 3; whereas the loin eye muscle depth 10 is the difference between the two boundary positions, fat-muscle boundary 3 and rib-muscle boundary 5. Exemplary automation algorithms for fat and loin depth are discussed in detail in the following discussions. The percentage of fat-free lean in pork muscle tissue is calculated using the fat depth and loin eye muscle depth as also discussed below.

Figure 10A:
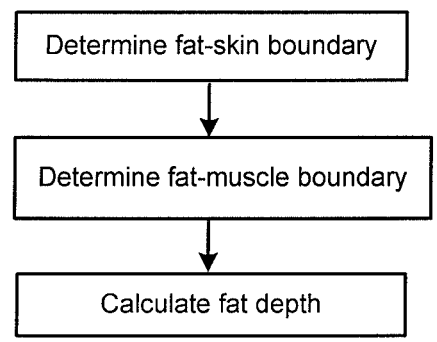
FIG. 10A shows a block diagram of an example fat depth automation algorithm, consistent with an example embodiment of the present invention.

Fat depth automation algorithms in accordance with certain embodiments include determining the two boundary positions, skin-fat and fat-muscle, from the ultrasound image of a swine carcass. FIG. 10A shows a block diagram of an example fat depth automation algorithm, which includes determining the fat-skin boundary, determining the fat-muscle boundary, and calculating the fat depth.

Threshold-based operations are used on the captured ultrasound image based on the horizontal resolution of grey level intensity to determine the desired boundary positions. First, the sum of grey level intensity along each row (horizontal resolution) and the entire image width (typically 640 pixels) is calculated. The sum is normalized with respect to the maximum of sum value. The row corresponding to a maximum value is the transducer-skin boundary. The intensity sum is scanned starting after a set number of pixel rows (e.g., 10) from the transducer-skin boundary until the end of the rows for the skin-fat boundary. A row with its intensity greater than a predefined threshold (e.g., 0.6) with a change in slope is determined. This row corresponds to the skin-fat boundary.

An image intensity histogram mean may be computed for sliding image strips of a predefined height (e.g., 13 pixels) and width that is the same as the actual tissue area (e.g., 500 pixels), for example, moving across the rows from the skin-fat boundary to bottom with a step size equal to half the strip height (e.g., 6 pixels). The starting row of each sliding image strip and its corresponding histogram mean are stored in an array. The strips corresponding to approximately 30 mm region (e.g., strips 1 to 25) covering the upper half of an image are processed further and the strip having a local maximum greater than a specific threshold (e.g., 0.8), and with a change in slope, is determined. As such, the selected strip should have the highest histogram mean greater than the threshold in this region, and this value should be higher than its consecutive previous and next strips. All the possible strips (1/2/3) corresponding to the three fat layers, satisfying the predefined threshold and change of slope criteria, are determined and combined in a group. The starting row of the last strip in this group corresponding to the third fat layer is assigned as the average row position for the fat-muscle boundary position. Fine adjustments are performed on this boundary position to get the closest fat-muscle boundary in the region between different pairs of ribs, at the same location as that of the loin depth measurements.

The fat depth may then be calculated as the difference between the two boundaries corresponding to skin-fat and fat-muscle. This difference is divided by a pixel-to-mm conversion ratio (e.g., 1 mm to 3.94 pixels) for the given equipment setting. There is also a difference in ultrasound velocities for the fat (e.g., 1430 m/s) and the scanner (e.g., 1540 m/s), and thus an adjustment factor may also be applied by multiplying the ratio of the velocities (e.g., 0.92857) by the calculated depth. For the values given above, the final fat depth formula is:

$$\text{Fat depth} = ((\text{Fat-muscle boundary row} - \text{Skin-fat boundary row})/3.94)*0.92857$$

Figure 10B:
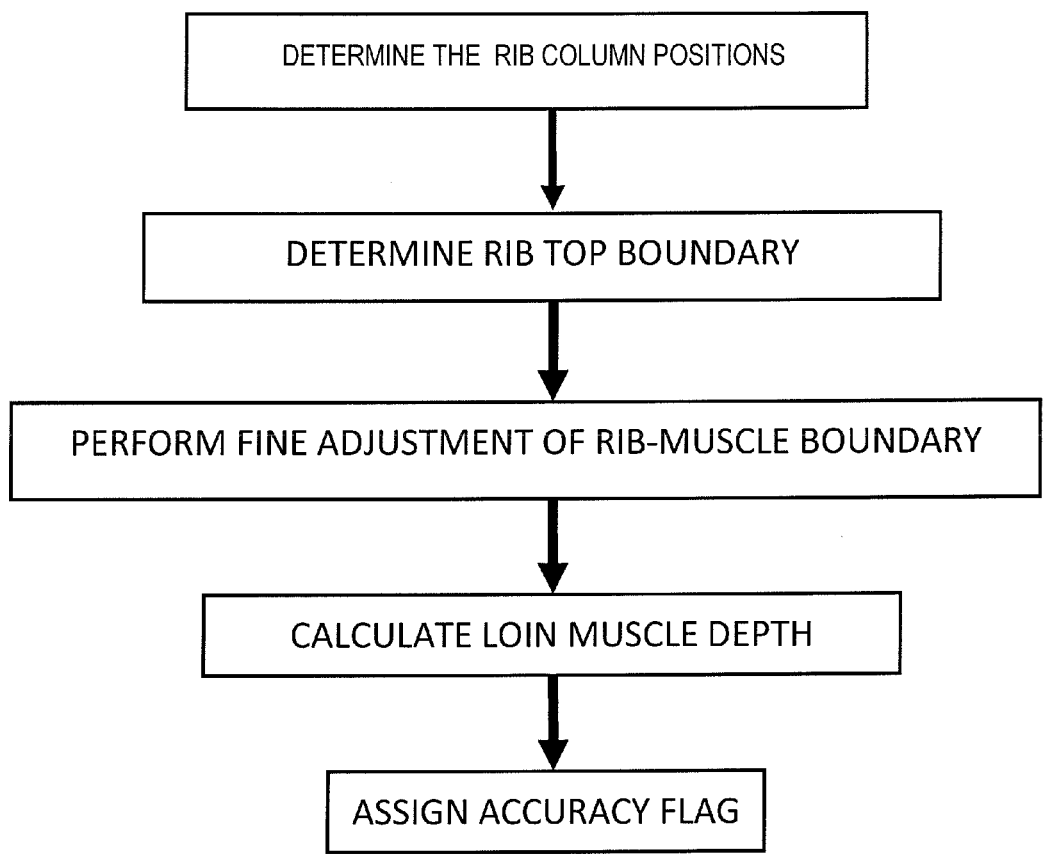
FIG. 10B shows a block diagram of an example loin depth automation algorithm, consistent with an example embodiment of the present invention.

An example algorithm for loin depth measurement proceeds as illustrated in the block diagram in FIG. 10B. First, the rib column positions for the first two ribs (labeled 6, 7, and 8 in FIG. 9) starting from the left side of the image are determined. Secondly, the rib top boundaries corresponding to these two rib columns are calculated. Then, these rib top boundaries are processed for fine adjustment to determine the boundary of the intercostales muscles. Finally, the loin eye muscle depth is calculated using the difference between the fat-muscle and the rib-muscle boundaries and proper pixel to mm conversion ratio for the particular study setup. The depth value is adjusted for a correction factor for ultrasound velocity in muscle tissue. An accuracy flag may be assigned to each depth measurement based on the image characteristics encountered in the algorithm to get the confidence level for the measurement. Each of these steps is discussed in detail below.

The fat and muscle tissue of a swine carcass indicated in an ultrasound image takes up only a portion of the image area (e.g., from rows 49 to 448 and columns 53 to 502 in a 640×480 pixel image). In a given image, a sub-image may be selected and considered for determining rib column positions for all the ribs from the left side of the image. Small sliding vertical strips (e.g., 10 pixels wide) are selected in the sub-image. The grey level intensity average is computed for each sliding strip. The starting column of each sliding strip and its corresponding intensity average is stored in an array. The array length is equal to the number of sliding strips in the sub-image.

The computed intensity average for sliding strips across columns is used to determine the rib column positions for the ribs starting from the left side of the image. The main focus to measure loin depth is between a pair of ribs due to the preferable position of image ROI for texture analysis for the prediction of IMF in the same region. There are some exceptions to this where the image may be dark in this region.

A group of strips starting from the left side of the image (e.g., the first 8 strips) from the column intensity average array are considered to determine the first rib column position. The strip having local minima of the intensity average with a change in slope is determined. The selected strip should have the lowest intensity average in this range, and its value should be lower than its consecutive previous and next strips. The starting column of this selected strip is assigned as the column position for the first rib. If the desired strip is not found, the first rib column position is assigned to zero. Since the two rib columns are not closer than approximately 100 pixels (e.g., 25 mm), the previous rib range is advanced by a predefined interval (e.g., 8 strips) and used as the range for the next rib. A similar procedure is performed to find a strip having local minima of the intensity average with a change in slope to determine the next rib column position. If the desired strip is not found, the rib column position is assigned to zero. This procedure is repeated to get all the possible rib column positions starting from the left side of the image.

After determining the first and second rib positions, the row corresponding to the rib top boundary for these two ribs are determined in the next step. Based on the possibilities of both the rib columns being zero or non-zero, there are 4 cases for calculating rib top boundary rows (refer to FIG. 9 for examples of Rib1 and Rib2 positions):

i) Rib1≠10 and Rib2≠0;
  ii) Rib1=0 and Rib2≠0;
  iii) Rib1≠0 and Rib2=0; and
  iv) Rib1=0 and Rib2=0.

In case (i), the rib top boundary is calculated for the two rib columns using the process described in detail below. The average of the two rib top boundary rows is calculated and the algorithm proceeds to the next step in order to perform some fine adjustments to get the closest rib-muscle boundary required for measurement of the loin eye muscle depth.

In cases (ii) and (iii), the rib top boundary for the non-zero rib value is calculated and the algorithm proceeds to the next step of fine adjustment.

In case (iv), the final rib-muscle boundary and loin eye muscle depth are both assigned to zero and an accuracy flag is set to indicate incorrect measurement and exit from the algorithm.

For every non-zero rib column 1 or 2, a sub-image is selected defined by the row starting from the fat-muscle boundary plus a set number of pixels, such as 120, to a set final row, such as row 420 (in mm conversion, fat-muscle boundary plus 30 mm to 105 mm). Within this sub-image a small moving image box of a set number of pixels (e.g., 13) high is selected starting from the bottom-most row. The width of this box is a set number of pixels (e.g., 30) covering the area in the vicinity of the respective rib column. The grey level intensity average of this image box is calculated. The image box is moved upwards along the rows with a step size of a set number of pixels (e.g., 6) and the intensity average is computed for all the image boxes in this sub-image. The starting row of each image box and its corresponding intensity average values are stored in an array. The box having local maxima of the intensity average with a change in slope is determined for the respective rib column. The starting row of this selected box is assigned to the rib top boundary position for the respective rib. If the desired box is not found, the rib top boundary position is assigned to the starting row of the local maxima irrespective of change in slope criteria. This procedure is performed for all non-zero rib column positions to determine respective rib top boundary positions.

In the next step, fine adjustments may be performed on the rib top boundary rows to obtain the closest row position near the rib-muscle boundary for the loin eye muscle depth. For example, the intercostales muscles area between the ribs is processed to get the closest point of the rib-muscle boundary. First, the average of rib top boundary rows for non-zero rib columns is computed. There are three possible cases for column range to perform fine adjustment based on rib column values with the step equal to a set number of pixels (e.g., 15) as below:
  i) If (Rib1≠0 and Rib2≠0), then the column range is from (Rib1−step) to (Rib2+step).
  ii) If (Rib1≠0 and Rib2=0), then the column range is from (Rib1−step) to (Rib1+step).
  iii) If (Rib1=0 and Rib2≠0), then the column range is from (Rib2−step) to (Rib2+step).

Once the column range is decided, the row range for fine adjustment is selected to the region with row position starting from average rib top boundary minus a set number of pixels (e.g., 35) to average rib position plus a set number of pixels (e.g., 30) which is around 8 mm up and down from the average rib top boundary. Then, starting from the top row, a small image strip (e.g., 8 pixels height and width equal to the column range) is considered and its average grey level intensity is computed. The strip is moved down (e.g., using a 4 pixel step size) until the bottom row is reached, and the same computation is performed for all the strips. The starting row of each image strip and its corresponding intensity average values are stored in an array. The difference between the intensity average values for each strip with its next consecutive strip is calculated. The starting row of the strip with the lowest negative difference is assigned to the final rib-muscle boundary row position required for the loin eye muscle depth measurement. If the desired strip is not found, the final rib-muscle boundary is assigned to the average rib-top boundary. This boundary corresponds to the top interface of the intercostales muscles.

To determine the bottom interface of the intercostales muscles, the row range is selected as the region with row position starting from the rib-muscle boundary plus a set number of pixels (e.g., 24) to the rib-muscle boundary plus a set number of pixels (e.g., 70) which is approximately 18 mm down from the rib-muscle boundary. The column range is the same as the one used for fine adjustment of the rib-muscle boundary. Then, starting from the top row, a small image strip (e.g., 13 pixels height and width equal to the column range), is considered, and its average grey level intensity is computed. The strip is moved down (e.g. using a 6 pixels step size) until the bottom row is reached, and the same computation is performed for all the strips. The starting row of each image strip and its corresponding intensity average values are stored in an array. The strip having local maxima of the intensity average with a change in slope is determined. The starting row of this selected strip is assigned to the bottom interface of the intercostales muscles. If the desired strip is not found, this boundary position is assigned to the starting row of the local maxima irrespective of the change in slope criteria. The user has the flexibility to measure the loin depth at a preferred location with respect to the intercostales muscles and the ribs. For example, one can measure loin depth up to the rib-muscle boundary (top interface of the intercostales muscles) or to the bottom interface of the intercostales muscles between any of the rib pairs.

For fine adjustment of the fat-muscle boundary, the row range for fine adjustment is selected as the region with row position starting from the average fat-muscle boundary minus a set number of pixels (e.g., 24) to the average fat boundary plus a set number of pixels (e.g., 24). This is around 6 mm up and down from the average fat-muscle boundary. The column range is the same as the one used for fine adjustment of the rib-muscle boundary. Then, starting from the top row, a small image strip (e.g., 13 pixels height and width equal to the column range), is considered, and its average grey level histogram mean is computed. The strip is moved down (e.g., using a 6 pixel step size) until the bottom row is reached, and the same computation is performed for all the strips. The starting row of each image strip and its corresponding histogram mean values are stored in an array. The difference in histogram mean values for each strip with its next consecutive strip is calculated. The starting row of the strip with the highest positive difference is assigned to the final fat-muscle boundary row position required for the fat depth measurement. If the desired strip is not found, the final fat-muscle boundary position is assigned to the average fat-muscle boundary.

Once the required rib-muscle and fat-muscle boundary positions are determined, the next step calculates the loin eye muscle depth based on the two boundary positions. An accuracy flag may also be assigned to indicate measurement accuracy. The loin eye muscle depth is the difference between the two boundaries corresponding to fat-muscle (determined in fat depth automation algorithm) and rib-muscle from the previous step. This difference is divided by the pixel to mm conversion ratio (e.g., 1 mm to 3.94 pixels) for the particular setup. For example, the final loin depth formula is: Loin eye muscle depth=((Fat-muscle boundary row−rib-muscle boundary row)/3.94)*1.025974.

In some cases, incorrect measurement for the loin eye muscle depth may result, for example due to high contrast, dark images, high echoes, unclear or deep down ribs, and blur that may cause false decisions on rib column position, rib top boundary row, and fine adjustment of rib-muscle boundary. Hence, an accuracy flag may be assigned to each measurement to indicate a confidence level. The flag may be assigned to '0' for correct and '1' for incorrect (or high probability of incorrect) measurement. This flag may be set to 1 based on the image characteristics encountered across the algorithm and are listed below:
  i) Rib1=0 and/or Rib2=0
  ii) Rib-muscle boundary=0
  iii) Rib-muscle boundary≧420 (i.e., last allowable line)
  iv) (Rib1−Rib2)>200 (i.e., largest allowable difference)
  v) (Rib1 top−Rib2 top)≧40 (i.e., largest allowable difference)
  vi) image histogram mean<45

The fat depth and loin eye muscle depth may be used to predict the percentage of fat-free lean in pork muscle tissue. The National Pork Producers Council has published six different equations for predicting fat-free lean based on the fat and muscle depth measurement system (NPPC, 2001). The equation given below calculates the percent fat-free lean based on the ultrasound fat and loin depth measurements.

$$\text{Perc\_lean} = ((15.31 + (0.51 * \text{hot carcass weight}) + (((3.813 * \text{loin depth}) - (31.277 * \text{fat depth}))/25.4))/ \text{hot carcass weight}) * 100$$

The number and diversity of the various embodiments show the surprising versatility and effectiveness of the devices and methods associated with embodiments of the present invention. For instance, the surprising effectiveness and accuracy of the developed image processing algorithms facilitates usage in a variety of applications and environments. In another instance, the flexibility to apply filters to the data and algorithms provides a surprisingly robust and efficient solution to a number of different problems. Thus, the embodiments disclosed herein should not be viewed as limiting and should be recognized as providing support for a variety of variations and related applications.

One such application relates to a method of assessing tissue characteristics or attributes in a portion of muscle tissue. The method includes selecting a region of interest within an image of the portion of muscle tissue; applying image texture processing to the region of interest; and extracting, responsive to the image texture processing, tissue characteristics or attributes of the portion of muscle tissue. The step of selecting a region of interest within an image of the portion of muscle tissue can include the use of fat and loin depth measurements and/or rib boundaries. In some instances, a set of texture parameters derived from images of the portion of muscle tissue can be used in combination with a prediction formula.

Other applications relate to one or more of the following. Regression modeling, statistical editing or pass filtering can be used in accordance with any embodiments of the present invention. Images can be filtered based upon one or more of pressure sensing, histogram thresholding, grey-scale gating, reflection intensities, blurriness, contrast levels, undesirable echo artifacts, and electromagnetic interference. Systems, algorithms or parameters can be normalized across a variety of devices and components. Automated positioning systems can be used for placement of an image probe/sensor on a portion of muscle tissue in accordance with a variety of embodiments. Different portions of muscle tissue can be sorted as a function of determined characteristics for portions of muscle tissue. The devices, methods, systems or arrangements of various embodiments of the invention can be applied to live animals, which can be useful for determining animal yield and quality calculations for the animals.

Aspects of the present invention lend themselves to implementations in a variety of devices including, but not limited to, hardware circuitry, programmable logic devices, firmware, software, and combinations thereof. A specific example includes computer readable medium storing computer executable instructions that when executed by a processor perform one or more of the process steps. The implementations of the various algorithms and methods described herein effectively transform what would otherwise be a general purpose processor into a specially-programmed processor that is configured and arranged to implement the specialized algorithms.

It should be apparent that the various methods and algorithms discussed herein represent more than abstract concepts and mental steps. For instance, embodiments of the present invention relate to the transformation of specific image-based content and include hardware interfaces with various input and output devices.

While the present invention has been described above and in the claims that follow, those skilled in the art will recognize that many changes may be made thereto without departing from the spirit and scope of the present invention. Such changes may include, for example, adjustments to various parameters or applications other than pork.

What is claimed is:

1. A system for measuring the relative content of intramuscular fat (IMF) in a portion of muscle tissue of a food animal, the system comprising:
   a probe configured and arranged to carry an ultrasound signal to the portion of muscle tissue;
   a mechanism configured and arranged to guide the probe to a desired location on the animal;
   an image sensor configured and arranged to generate image data from the ultrasound signal;
   a pressure sensor configured and arranged to sense pressure being exerted between the probe and the animal; and
   a data processor configured and arranged to measure the relative content of IMF in the portion of muscle tissue by processing the image data as a function of the sensed pressure, and to measure the relative content of IMF in the portion of muscle tissue using parameters that include Fourier intensity coefficient of variation, a ratio of Fourier powers within a first normalized freq range, a ratio of Fourier powers within a second normalized freq range, pixel grey scale histogram skew value, pixel grey scale histogram standard deviation and pixel grey scale histogram coefficient of variation.

2. A method of measuring percent lean in a food animal, the method comprising:
   presenting an ultrasound signal to a tissue region of the food animal using a probe;
   capturing image data corresponding to a plurality of image frames of the tissue region from the ultrasound signal;
   performing filter-based editing of the captured plurality of image frames;
   determining image-based landmarks and tissue interfaces, including boundary positions of fat, muscle, and ribs in the tissue, from the filtered plurality of image frames;
   calculating fat depth and muscle depth parameters by applying a statistical filter to image frames representing image data corresponding to the portion of muscle tissue, the statistical filter calculating the parameters using one or more of: a Fourier intensity coefficient of variation, a ratio of Fourier powers within a first normalized frequency range, a ratio of Fourier powers within a second normalized frequency range, pixel grey scale histogram skew value, pixel grey scale histogram standard deviation and pixel grey scale histogram coefficient of variation; and
   measuring the percent lean in the food animal as a function of the calculated fat depth and muscle depth parameters using a pressure sensor and the statistical filter; wherein the pressure sensor configured and arranged to sense pressure being exerted between the probe and the animal, such as excluding various images that do not meet the pressure criteria.

* * * * *